(12) United States Patent
Ikeda et al.

(10) Patent No.: US 8,975,411 B2
(45) Date of Patent: Mar. 10, 2015

(54) THERAPEUTIC AGENT FOR NEUROLOGICAL DISEASES

(75) Inventors: Joh-E Ikeda, Tokyo (JP); Noriaki Hirayama, Isehara (JP); Satoshi Inoue, Akitakata (JP); Kazunori Tanaka, Tokyo (JP); Takuya Kanno, Tokyo (JP)

(73) Assignees: Neugen Pharma Inc., Tokyo (JP); Wakunaga Pharmaceutical Co., Ltd., Osaka-shi (JP)

( * ) Notice: Subject to any disclaimer, the term of this patent is extended or adjusted under 35 U.S.C. 154(b) by 1 day.

(21) Appl. No.: 13/812,726

(22) PCT Filed: Jul. 15, 2011

(86) PCT No.: PCT/JP2011/066214
§ 371 (c)(1),
(2), (4) Date: Apr. 9, 2013

(87) PCT Pub. No.: WO2012/014699
PCT Pub. Date: Feb. 2, 2012

(65) Prior Publication Data
US 2013/0190363 A1    Jul. 25, 2013

(30) Foreign Application Priority Data
Jul. 28, 2010 (JP) ................. 2010-169460

(51) Int. Cl.
| | | |
|---|---|---|
| C07D 401/04 | (2006.01) | |
| C07D 401/14 | (2006.01) | |
| C07D 217/00 | (2006.01) | |
| C07D 217/02 | (2006.01) | |
| C07D 233/00 | (2006.01) | |
| C07D 233/88 | (2006.01) | |

(52) U.S. Cl.
CPC ............ C07D 401/04 (2013.01); C07D 233/88 (2013.01)
USPC ........ 546/274.1; 514/307; 514/341; 514/398; 546/144; 548/332.5

(58) Field of Classification Search
None
See application file for complete search history.

(56) References Cited

U.S. PATENT DOCUMENTS

| | | |
|---|---|---|
| 6,617,429 B1 | 9/2003 | Ikeda et al. |
| 2005/0100997 A1 | 5/2005 | Ikeda et al. |
| 2005/0176789 A1 | 8/2005 | Hadida Ruah et al. |
| 2005/0261306 A1 | 11/2005 | Ikeda et al. |
| 2009/0275592 A1* | 11/2009 | Zeng et al. ............... 514/252.05 |

FOREIGN PATENT DOCUMENTS

| | | |
|---|---|---|
| JP | 11 116599 | 4/1999 |
| JP | 2004 123562 | 4/2004 |
| JP | 2008 13446 | 1/2008 |
| WO | 2005 026137 | 3/2005 |
| WO | 2008 050600 | 5/2008 |
| WO | WO 2008/057862 A2 * | 5/2008 |
| WO | 2008 101029 | 8/2008 |
| WO | 2008 124000 | 10/2008 |

OTHER PUBLICATIONS

Ikeda, KV. et al. A Novel Acylaminoimidazole Derivative, WN1316, Alleviates Disease Progression via Suppression of Glial Inflammation in ALS Mouse Model. PLOS ONE. 2014, vol. 9, p. e87728.*
Carlsson, J. et al. Structure-Based Discovery of A2A Adenosine Receptor Ligands. J. Med. Chem. 2010, vol. 53, p. 3751.*
Kagaku Daijiten Henshu linkai, "Kagaku Daijiten 1," Kyoritsu Shuppan Co., Ltd., Total pages 4, (1987) (with English translation).
Kagaku Daijiten Henshu linkai, "Kagaku Daijiten 5," Kyoritsu Shuppan Co., Ltd., Total pages 4, (1987) (with English translation).
Roy, N. et al., "The Gene for Neuronal Apoptosis Inhibitory Protein Is Partially Deleted in Individuals with Spinal Muscular Atrophy," Cell, vol. 80, pp. 167 to 178, (Jan. 13, 1995).
Okada, Y. et al., "A dopamine D4 receptor antagonist attenuates ischemia-induced neuronal cell damage via upregulation of neuronal apoptosis inhibitory protein," Journal of Cerebral Blood Flow & Metabolism, vol. 25, pp. 794 to 806, (2005).
International Search Report Issued Sep. 6, 2011 in PCT/JP11/66214, Filed Jul. 15, 2011.

* cited by examiner

*Primary Examiner* — Rita Desai
*Assistant Examiner* — Ben S Michelson
(74) *Attorney, Agent, or Firm* — Oblon, McClelland, Maier & Neustadt, L.L.P.

(57) ABSTRACT

An object of the present invention is to provide a pharmaceutical agent useful for treating and preventing neurological disease, having satisfactory solubility and oxidative stress-mediated cell death suppressive activity as well as capable of exhibiting excellent blood-brain barrier permeability. The present invention is directed to an acylaminoimidazole derivative represented by general formula (I) or a salt thereof, and a pharmaceutical and a therapeutic or preventive agent for neurological disease containing the same, as an active ingredient.

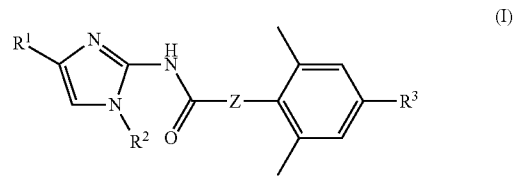

15 Claims, 5 Drawing Sheets

THERAPEUTIC AGENT FOR NEUROLOGICAL DISEASES

This application is a National Stage of PCT/JP11/066,214 filed Jul. 15, 2011 and claims the benefit of JP 2010-169460 filed Jul. 28, 2010.

TECHNICAL FIELD

The present invention relates to a therapeutic or preventive agent for neurological disease using a novel acylaminoimidazole derivative or a salt thereof.

BACKGROUND ART

A group of neurological diseases in which degeneration of neural cells is involved, such as amyotrophic lateral sclerosis (ALS), spinal muscular atrophy (SMA), Huntington's disease, Parkinson's disease, Alzheimer's disease, dementia after a cerebrovascular disorder, and dementia accompanying other neurological deficits, is generally called neurodegenerative diseases. Almost all the neurodegenerative diseases have no established fundamental therapeutic method and thus research for therapeutic method has been desired.

For example, as a therapeutic approach for neurodegenerative disease, administration of a factor suppressing degeneration of nerve cells is conceivable. Administration of a factor suppressing neurodegeneration is expected to bring an advantageous effect on therapy and prevention of such disease. However, such a factor, which can be actually and effectively used as a therapeutic agent, has virtually not been found.

As the factor suppressing degeneration of nerve cells, for example, it is known that a certain type of dopamine receptor agonist possibly has such a function. However, whether there is a causal relation between dopamine antagonism and suppression of nerve-cell degeneration is not known. In addition, it has not always been true that all dopamine receptor agonists have such a function.

In contrast, as a modifying factor for the severity of spinal muscular atrophy (SMA), one of intractable neurodegenerative diseases of the lower motor neuron, a neuronal apoptosis inhibitory protein (NAIP) gene was isolated from human chromosomal 5q13.1 region (see Non Patent Literature 1) and the entire amino acid sequence of NAIP and cDNA encoding NAIP were isolated (see Patent Literature 1). In addition, it was found that, in the process for searching a substance increasing NAIP production, some dopamine receptor antagonists increase the NAIP production, and that these can actually suppress neural degeneration (see Patent Literature 2). Furthermore, it is known that similar dopamine receptor antagonists can protect nerve cells and non-nerve cells from apoptosis caused by oxidative stress and suppress nerve cell death caused by ischemia (see Non Patent Literature 2).

Based on the oxidative stress hypothesis, clinical studies using vitamin E, creatine and others were carried out, however, all attempts failed. In the circumstance, various types of active compounds which increase endogenous NAIP production and suppress oxidative stress-mediated cell death were found (see Patent Literature 3, for example, a compound represented by the following formula (X)).

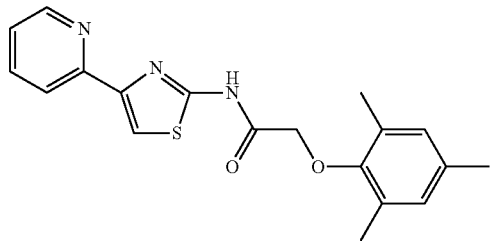

(X)

In the meantime, to sufficiently show the efficacy of a medicinal substance in treating neurological disease, particularly brain neurodegenerative disease, bioavailability thereof must be high. As a more preferred property, blood-brain barrier permeability is desirably high. However, even the aforementioned various types of active compounds capable of suppressing oxidative stress-mediated cell death still have much to be improved, in view of improvement of the solubility and further improvement of the blood-brain barrier permeability.

CITATION LIST

Patent Literatures

Patent Literature 1: JP-A-11-116599
Patent Literature 2: JP-A-2004-123562
Patent Literature 3: International Publication No. WO 2008/050600

Non Patent Literatures

Non Patent Literature 1: Roy M. et al. Cell (1995) 80, 167-178
Non Patent Literature 2: Okada Y. et al. Journal of Cerebral Blood Flow & Metabolism (2005) 25, 794-806

SUMMARY OF THE INVENTION

Technical Problem

The present invention provides a pharmaceutical agent useful for treating and preventing neurological disease, having satisfactory solubility, suppressive activity of oxidative stress-mediated cell death and capable of exhibiting excellent blood-brain barrier permeability.

Solution to Problem

The present inventors found that a novel acylaminoimidazole derivative having a specific structure containing an imidazole group or a salt thereof is extremely useful as a pharmaceutical agent having both excellent suppressive activity of oxidative stress-mediated cell death and blood-brain barrier permeability while retaining satisfactory solubility. Based on the finding, the present invention was accomplished.

More specifically, the present invention relates to the following 1) to 9).

1) An acylaminoimidazole derivative represented by the general formula (I) or a salt thereof:

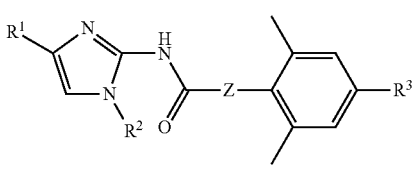

wherein R¹ represents a group represented by the following formula (Ia) or (Ib):

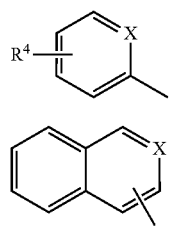

wherein R⁴ represents a hydrogen atom, a hydroxy group, a nitro group, an optionally substituted amino group, an alkyl group or alkoxy group having 1 to 6 carbon atoms, or an optionally substituted aryl group, an aralkyl group or an aralkyloxy group; and X represents —CH— or a nitrogen atom, R² and R³ each independently represent a hydrogen atom or an alkyl group having 1 to 6 carbon atoms, and Z represents a group represented by the following formula (Ic) or (Id):

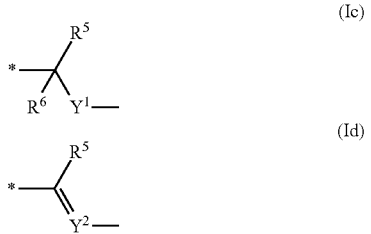

wherein R⁵ and R⁶ each independently represent a hydrogen atom or an alkyl group having 1 to 6 carbon atoms, in which R⁵ and R⁶ may be joined together to form a 3 to 6-membered ring, $Y^1$ represents an oxygen atom, a sulfur atom, —CH₂— or —NR⁷—, in which R⁷ represents a hydrogen atom or an alkyl group having 1 to 6 carbon atoms; and $Y^2$ represents a nitrogen atom or —CH—, (note that * represents a site binding to the carbonyl group;

with the proviso that a compound wherein R¹ is a group represented by the formula (Ia); R² is a hydrogen atom; R³ is a methyl group; and Z is a group represented by the formula (Ic); in the formula (Ia) R⁴ is a hydrogen atom and X is a nitrogen atom and, in the formula (Ic) $Y^1$ is an oxygen atom and R⁵ and R⁶ are hydrogen atoms is excluded.

2) The acylaminoimidazole derivative or a salt thereof, wherein, in the above formula (I) R¹ is a group represented by the above formula (Ia); and, in the formula (Ia) R⁴ is a hydrogen atom and X is a nitrogen atom.

3) The acylaminoimidazole derivative or a salt thereof, wherein the acylaminoimidazole derivative represented by the above formula (I) is (2R)-2-(mesityloxy)-N-[4-(pyridin-2-yl)-1H-imidazol-2-yl]propanamide; 2-(mesitylamino)-N-[4-(pyridin-2-yl)-1H-imidazol-2-yl]acetamide or 2-[mesityl(methyl)amino]-N-[4-(pyridin-2-yl)-1H-imidazol-2-yl]acetamide.

4) A pharmaceutical comprising the acylaminoimidazole derivative or a salt thereof as an active ingredient.

5) A therapeutic or preventive agent for neurological disease comprising the acylaminoimidazole derivative or a salt thereof as an active ingredient.

6) An oxidative stress-mediated cell death suppressant comprising the acylaminoimidazole derivative or a salt thereof as an active ingredient.

7) The therapeutic or preventive agent for neurological disease, wherein the neurological disease is neurodegenerative disease having cell degeneration due to oxidative stress as a molecular background or neurological disease mainly caused by nerve cell death.

8) A pharmaceutical composition comprising the acylaminoimidazole derivative or a salt thereof and a pharmaceutically acceptable carrier.

9) Use of the acylaminoimidazole derivative or a salt thereof for manufacturing a pharmaceutical.

10) The acylaminoimidazole derivative or a salt thereof for use in prevention or treatment of neurological disease.

11) The acylaminoimidazole derivative or a salt thereof, wherein the neurological disease is neurodegenerative disease having cell degeneration due to oxidative stress as a molecular background or neurological disease mainly caused by nerve cell death.

12) A therapeutic or preventive method for neurological disease, comprising administering the acylaminoimidazole derivative or a salt thereof to a patient in need thereof.

13) The therapeutic or preventive method for neurological disease, wherein the neurological disease is neurodegenerative disease having cell degeneration due to oxidative stress as a molecular background or neurological disease mainly caused by nerve cell death.

Advantageous Effects of Invention

The acylaminoimidazole derivative of the present invention or a salt thereof has both extremely excellent suppressive activity of oxidative stress-mediated cell death and blood-brain barrier permeability while having satisfactory solubility, and is extremely useful as an therapeutic or preventive agent for neurological disease, more specifically, not only amyotrophic lateral sclerosis (ALS) but also familial and sporadic neurodegenerative diseases of the upper/lower motor neurons including spastic paraplegia (SPG), primary lateral sclerosis (PLS), bulbar paralysis, paraplegia, and spinal muscular atrophy (SMA). In addition, the acylaminoimidazole derivative of the present invention or a salt thereof is also extremely useful as an therapeutic or preventive agent for neurodegenerative disease having cell degeneration due to oxidative stress as a molecular background and neurological disease mainly caused by nerve cell death, more specifically, neurodegenerative diseases of the peripheral and central nervous systems such as multiple system atrophy (MSA), Alzheimer's disease, Parkinson's disease and senile cognitive disorder.

DESCRIPTION OF EMBODIMENTS

Figure 1:
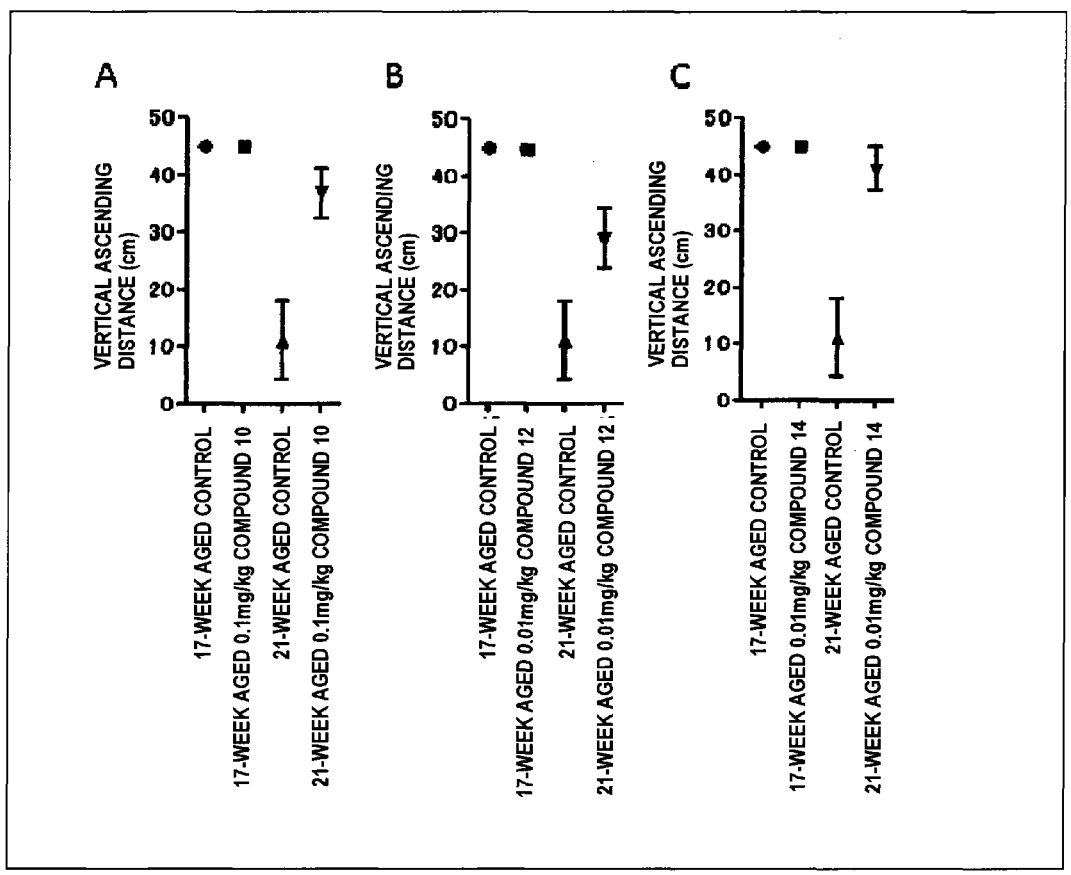
FIG. 1 is a graph showing the results of a vertical pole test in ALS-SOD1$^{H46R}$ mice to which compound 10, compound 12 and compound 14 were administered. A, B, and C indicate the administration results for compound 10, compound 12, and compound 14, respectively.

The present invention will be described in detail, below.

Note that, in the specification, the "neurological disease" includes neurodegenerative diseases due to oxidative stress-mediated cell death as a molecular background. The "neurodegenerative disease" refers to neurological disease caused by gradual death of a specific group of nerve cells present in the central nerve.

The "neurodegenerative disease due to oxidative stress-mediated cell death as a molecular background" refers to neurodegenerative disease of which cell death due to oxidative stress is the molecular background. The "molecular background", which refers to "pathogenesis/pathological conditions", indicates a cause of disease or the course of disease.

Examples of the above neurological diseases include not only amyotrophic lateral sclerosis (ALS) but also familial and sporadic neurodegenerative diseases of the upper/lower motor neurons including spastic paraplegia (SPG), primary lateral sclerosis (PLS), bulbar paralysis, paraplegia and spinal muscular atrophy (SMA). Examples of the neurological diseases further include neurological diseases mainly caused by neurodegeneration having oxidative stress-mediated cell death as a molecular background and nerve cell death, more specifically, neurodegenerative diseases of the peripheral and central nervous systems such as multiple system atrophy (MSA), Alzheimer's disease, Parkinson's disease and senile cognitive disorder.

In general formula (I), $R^1$ represents a group represented by the following formula (Ia) or (Ib).

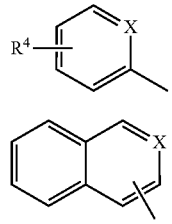

(Ia)

(Ib)

Herein, X represents —CH— or a nitrogen atom, preferably represents a nitrogen atom in the case where $R^1$ represents a group represented by formula (Ia) and represents —CH— in the case where $R^1$ represents a group represented by formula (Ib).

Examples of the substituent for an amino group represented by $R^4$ include an alkyl group having 1 to 6 carbon atoms, an allyl group, a formyl group and an acyl group. Specific examples thereof include a methylamino group, an ethylamino group, a propylamino group, a butylamino group, a dimethylamino group, a vinylamino group, an allylamino group, a formylamino group, an acetylamino group and a propionylamino group.

The alkyl group having 1 to 6 carbon atoms represented by $R^4$ may be either a linear chain or a branched chain having 3 to 6 carbon atoms. Specific examples thereof include a methyl group, an ethyl group, a propyl group, an isopropyl group, a butyl group, an isobutyl group, a tert-butyl group, a pentyl group and a hexyl group. Of them, a linear chain having 1 to 3 carbon atoms or a branched chain having 3 carbon atoms such as a methyl group, an ethyl group, a propyl group and an isopropyl group is preferable, and particularly a methyl group is preferable.

Specific examples of the alkoxy group having 1 to 6 carbon atoms represented by $R^4$ include a methoxy group, an ethoxy group, a n-propoxy group, an i-propoxy group, a n-butoxy group and a tert-butoxy group.

As the aryl group represented by $R^4$, a group of an aromatic ring having 6 to 10 carbon atoms is mentioned. The hydrogen atoms on the ring may be substituted with a hydroxy group, a nitro group, an amino group, an acylamino group, an alkoxy group and the like. Specific examples thereof include a phenyl group, a hydroxyphenyl group, a nitrophenyl group, an aminophenyl group, an acetylaminophenyl group, a methoxyphenyl group and an ethoxyphenyl group.

Examples of the aralkyl group represented by $R^4$ include a benzyl group and a phenylethyl group.

Examples of the aralkyloxy group represented by $R^4$ include a benzyloxy group and a methoxybenzyloxy group.

Of these aryl groups, aralkyl groups and aralkyloxy groups, a phenyl group is preferable.

Herein, the group formed of the condensed aromatic ring represented by formula (Ib) is preferably bound to the 4-position of an imidazole ring at the 1-position or 2-position of the condensed aromatic ring. Examples of such a group include a 1-naphthyl group and a 2-naphthyl group in the case where X is —CH—.

Note that, in formula (I), as $R^1$, a group represented by formula (Ia) is preferable.

In the above formula (I), as the alkyl groups represented by $R^2$ and $R^3$, the same groups as exemplified as the alkyl group represented by $R^4$ may be mentioned. As $R^2$, a hydrogen atom is preferable. As $R^3$, a hydrogen atom or a methyl group is preferable.

In the above formula (I), Z represents a group represented by the following formula (Ic) or (Id).

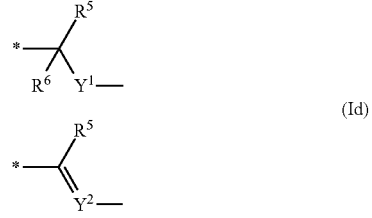

In formulae (Ic) and (Id), * represents a site in Z binding to a carbonyl group. As the alkyl groups represented by $R^5$ and $R^6$, the same groups as exemplified as the alkyl group represented by $R^4$ may be mentioned. Furthermore, $R^5$ and $R^6$ may be joined together to form a 3 to 6-membered ring, preferably a 3 to 4-membered ring such as a cyclopropane ring or a cyclobutane ring. As $R^5$ and $R^6$, a hydrogen atom or a methyl group is preferable.

In formula (Ic), $Y^1$ represents an oxygen atom, a sulfur atom, —$CH_2$— or —$NR^7$— (in which $R^7$ is a hydrogen atom or an alkyl group having 1 to 6 carbon atoms). As the alkyl group represented by $R^7$, the same groups as exemplified as the alkyl group represented by $R^4$ may be mentioned. As $Y^1$, an oxygen atom or —$NR^7$— (in which $R^7$ is a hydrogen atom or a methyl group) is preferable.

In formula (Id), $Y^2$ represents a nitrogen atom or —CH—, preferably —CH—.

Note that, as Z in formula (I), a group represented by formula (Ic) is preferable.

Note that, of the compounds represented by the above formula (I), a compound wherein $R^1$ is a group represented by formula (Ia), $R^2$ is a hydrogen atom, $R^3$ is a methyl group, and Z is a group represented by formula (Ic), in formula (Ia) $R^4$ is a hydrogen atom and X is a nitrogen atom, in formula (Ic) $Y^1$ is an oxygen atom, and $R^5$ and $R^6$ are hydrogen atoms, in short, a compound represented by the following formula (Ie), is excluded. Such a compound is not included in the acylaminoimidazole derivative of the present invention.

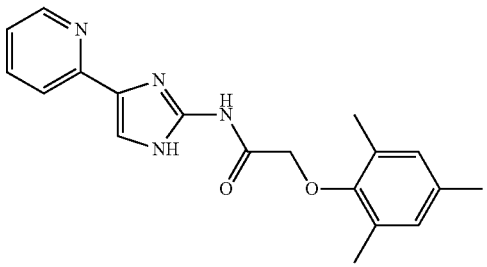

(Ie)

More preferred compounds of the acylaminoimidazole derivative represented by the above formula (I) include 1) a compound wherein $R^1$ is a group represented by the above formula (Ia), and in the formula (Ia) $R^4$ is a hydrogen atom and X is a nitrogen atom;

2) a compound wherein $R^1$ is a group represented by the above formula (Ia), and in the formula (Ia) $R^4$ is a phenyl group and X is a nitrogen atom;

3) a compound wherein $R^1$ is a group represented by the above formula (Ia), in the formula (Ia) $R^4$ is a hydrogen atom and X is a nitrogen atom, Z is a group represented by the above formula (Ic), and in the formula (Ic) $R^5$ and $R^6$ are each a hydrogen atom or a methyl group;

4) a compound wherein $R^1$ is a group represented by the above formula (Ia), in the formula (Ia) $R^4$ is a hydrogen atom and X is a nitrogen atom, Z is a group represented by the above formula (Ic), in the formula (Ic) $R^5$ and $R^6$ are each a hydrogen atom or a methyl group and $R^3$ is a hydrogen atom or a methyl group;

5) a compound wherein $R^1$ is a group represented by the above formula (Ia), in the formula (Ia) $R^4$ is a hydrogen atom and X is a nitrogen atom, Z is a group represented by the above formula (Ic), in the formula (Ic) $R^5$ and $R^6$ are each a hydrogen atom or a methyl group, $R^3$ is a hydrogen atom or a methyl group and in the formula (Ic) $Y^1$ is an oxygen atom or —$NR^7$— ($R^7$ is a hydrogen atom or a methyl group).

Examples of a particularly preferred compound of the acylaminoimidazole derivative represented by the above formula (I) include (2R)-2-(mesityloxy)-N-[4-(pyridin-2-yl)-1H-imidazol-2-yl]propanamide, 2-(mesitylamino)-N-[4-(pyridin-2-yl)-1H-imidazol-2-yl]acetamide and 2-[mesityl(methyl)amino]-N-[4-(pyridin-2-yl)-1H-imidazol-2-yl]acetamide.

Examples of a salt of the acylaminoimidazole derivative represented by the above formula (I) include an acid addition salt and a base addition salt formed of the acylaminoimidazole derivative (I) and an acid or a base. Examples of the acid addition salt include salts formed of the acylaminoimidazole derivative (I) and (a) a mineral acid such as hydrochloric acid or sulfuric acid; salts formed of the acylaminoimidazole derivative (I) and (b) an organic carboxylic acid such as formic acid, acetic acid, citric acid, trichloroacetic acid, trifluoroacetic acid, fumaric acid or maleic acid; and salts formed of the acylaminoimidazole derivative (I) and (c) a sulfonic acid such as methanesulfonic acid, benzenesulfonic acid, p-toluenesulfonic acid, mesitylenesulfonic acid or naphthalenesulfonic acid.

Examples of the base addition salt include salts formed of the acylaminoimidazole derivative as mentioned above and (a') an alkaline metal such as sodium and potassium, salts formed of the acylaminoimidazole and (b') an alkaline earth metal such as calcium or magnesium, salts formed of the acylaminoimidazole derivative and (c') an ammonium; and salts formed of the acylaminoimidazole derivative and (d') a nitrogen-containing organic base such as trimethylamine, triethylamine, tributylamine, pyridine, N,N-dimethylaniline, N-methyl-D(-)-glucamine, N-methylpiperidine, N-methylmorpholine, diethylamine, cyclohexylamine, procaine, dibenzylamine, N-benzyl-3-phenethylamine, 1-ephenamine or N,N'-dibenzylethylenediamine.

Furthermore, the acylaminoimidazole derivative or a salt thereof as mentioned above can be present not only as an unsolvated form but also as a hydrate or a solvate. Accordingly, in the present invention, all crystal types and hydrates or solvates thereof are included.

Furthermore, if the acylaminoimidazole derivative as mentioned above has an enantiomer and a diastereomer, all of these stereoisomers are included.

The acylaminoimidazole derivative as mentioned above can be produced, for example, by the following method.

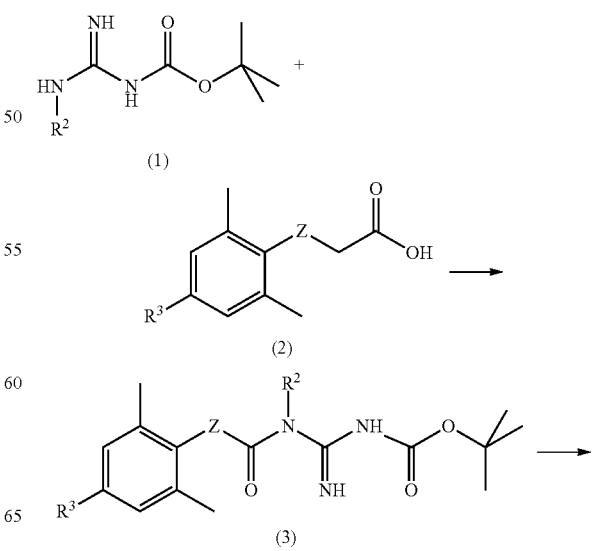

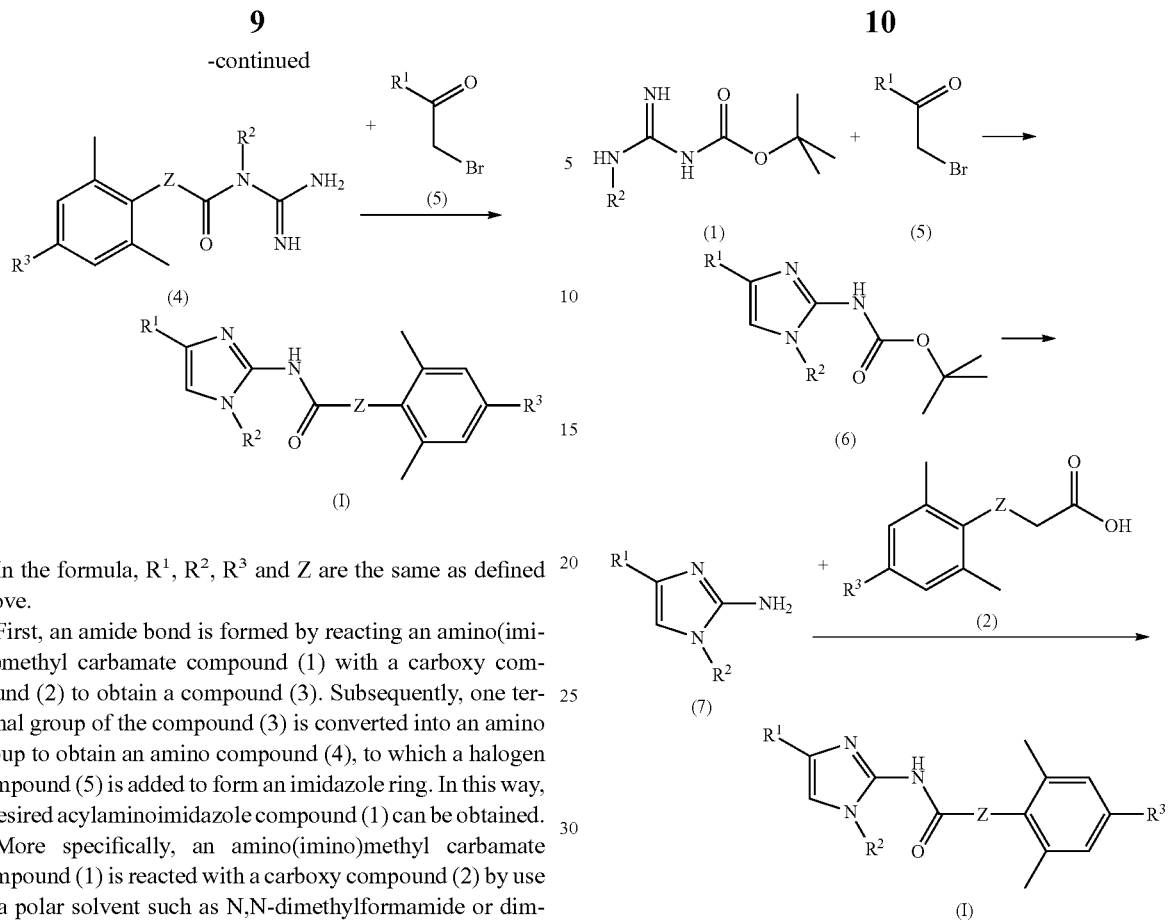

In the formula, $R^1$, $R^2$, $R^3$ and Z are the same as defined above.

First, an amide bond is formed by reacting an amino(imino)methyl carbamate compound (1) with a carboxy compound (2) to obtain a compound (3). Subsequently, one terminal group of the compound (3) is converted into an amino group to obtain an amino compound (4), to which a halogen compound (5) is added to form an imidazole ring. In this way, a desired acylaminoimidazole compound (I) can be obtained.

More specifically, an amino(imino)methyl carbamate compound (1) is reacted with a carboxy compound (2) by use of a polar solvent such as N,N-dimethylformamide or dimethyl sulfoxide. The amount of compound (1) used usually ranges 0.01 to 2.00 mol/L, preferably 0.20 to 0.50 mol/L. The amount of carboxy compound (2) used usually ranges 0.01 to 2.20 mol/L, preferably 0.22 to 0.55 mol/L. Subsequently, the reaction is performed at a temperature of usually 10 to 80° C., preferably 10 to 40° C. in the presence of a basic compound and a reagent for forming an amide bond such as 2-(1H-benztriazol-1-yl)-1,1,3,3-tetramethyluronium hexafluorophosphate. The reaction time is usually 2 to 48 hours, preferably 12 to 24 hours.

In obtaining an amino compound (4) by reacting compound (3), anisole and trifluoroacetic acid or others are added and then stirred usually at a temperature of 0 to 70° C., preferably 20 to 70° C., usually for 1 to 12 hours, preferably 2 to 5 hours. Extraction is performed with a solvent such as chloroform or carbon tetrachloride.

The obtained amino compound (4) is dissolved in a polar solvent such as N,N-dimethylformamide or dimethyl sulfoxide, to which a halogen compound (5) is added. At this time, the use amount of amino compound (4) is usually 0.1 to 2.0 mol/L, preferably 0.3 to 1.0 mol/L and the use amount of halogen compound (5) is usually 0.03 to 0.70 mol/L, preferably 0.10 to 0.33 mol/L. Subsequently, the reaction mixture is stirred usually at a temperature of 10 to 40° C., preferably 20 to 30° C. and usually for 24 to 200 hours, preferably 72 to 120 hours and then extracted with ethyl acetate or the like to obtain the acylaminoimidazole compound (I).

Also, the acylaminoimidazole compound (I) can be produced by a method starting from formation of an imidazole ring, as shown below.

In the formula, $R^1$, $R^2$, $R^3$ and Z are the same as defined above.

First, to an amino(imino)methyl carbamate compound (1), a halogen compound (5) is added to form an imidazole ring. In this manner, a compound (6) is obtained. Subsequently, one terminal of the compound (6) is converted into an amino group to obtain an amino compound (7), which is reacted with a carboxy compound (2) to form an amide bond. In this way, a desired acylaminoimidazole compound (I) can be obtained. The solvent, reagents used in individual reactions herein and use amounts thereof can be the same as those of the aforementioned method.

Note that, to obtain the above amino compound (7), the method shown below may be used to form an imidazole ring.

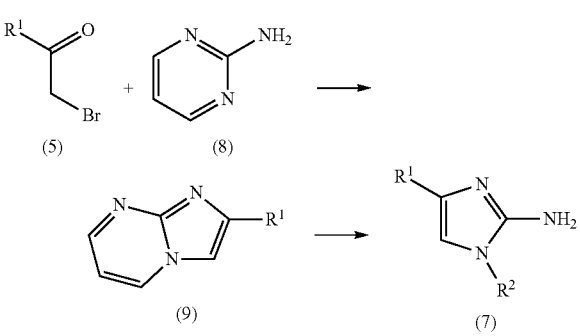

In the formula, $R^1$, $R^2$, $R^3$ and Z are the same as defined above.

The halogen compound (5) as mentioned above and 2-aminopyrimidine (8) are dissolved in a solvent such as ethanol and heated to obtain an imidazopyrimidine compound (9). Subsequently, the imidazopyrimidine compound (9) and hydrazine are heated in a solvent such as ethanol to obtain an amino compound (7). At this time, the use amount of halogen compound (5) is usually 0.1 to 2.0 mol/L, preferably 0.5 to 1.0 mol/L. The use amount of 2-aminopyrimidine (8) is usually 0.1 to 2.0 mol/L, preferably 0.5 to 1.0 mol/L. The reaction solution is stirred usually at a temperature of 30 to 80° C., preferably 60 to 80° C. and usually for 3 to 24 hours, preferably 10 to 15 hours to obtain the imidazopyrimidine compound (9). The obtained imidazopyrimidine compound (9) in the use amount of usually 0.1 to 0.5 mol/L, preferably 0.2 to 0.3 mol/L and hydrazine (the use amount thereof is usually 0.4 to 2.0 mol/L and preferably 0.8 to 1.2 mol/L) are heated to reflux for 2 to 24 hours and preferably 10 to 15 hours, followed by azeotropic removal with ethanol or the like.

The acylaminoimidazole compound (I) obtained by the above method can be also used to obtain a desired acylaminoimidazole compound (I) by appropriately converting a substituent. Also, the acylaminoimidazole compound (I) can be produced by appropriately combining other methods.

Since the acylaminoimidazole derivative or a salt thereof thus obtained efficiently has satisfactory suppressive activity of oxidative stress-mediated cell death which a conventional active compound such as a compound represented by the following formula (X) and described in Patent Literature 3 has, it can sufficiently exert the activity in vivo. In addition, since the acylaminoimidazole derivative or a salt thereof also has extremely excellent blood-brain barrier permeability compared to the compound, a pharmaceutical agent, which can remarkably improve blood-brain barrier permeability compared to conventional agents, can be realized. The acylaminoimidazole derivative (I) is a compound improved in suppressive activity of oxidative stress-mediated cell death as well as improved in solubility by converting a thiazole group of the following formula (X) into an imidazole group, and further, significantly improved in blood-brain barrier permeability by introducing a predetermined substituent.

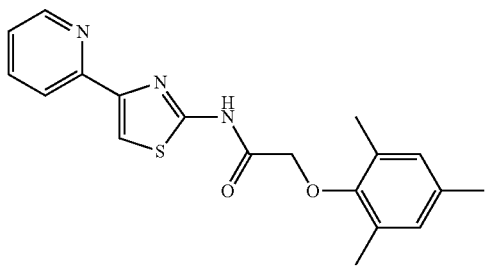

(X)

Accordingly, the acylaminoimidazole derivative (I) or a salt thereof is useful as pharmaceutical, animal drugs and others for preventing or treating neurological diseases, principally neurodegenerative diseases due to oxidative stress-mediated cell death as a molecular background, particularly, brain neurodegenerative diseases.

Examples of the neurological diseases include not only amyotrophic lateral sclerosis (ALS) but also familial and sporadic neurodegenerative diseases of the upper/lower motor neurons such as spastic paraplegia (SPG), primary lateral sclerosis (PLS), bulbar paralysis, paraplegia and spinal muscular atrophy (SMA). In addition, neurological disease mainly caused by neurodegeneration having oxidative stress-mediated cell death as a molecular background and nerve cell death, for example, neurodegenerative diseases of the peripheral and central nervous systems such as multiple system atrophy (MSA), Alzheimer's disease, Parkinson's disease and senile cognitive disorder are included.

In the case where the acylaminoimidazole derivative of the present invention or a salt thereof is used as a pharmaceutical, as an agent for preventing or treating neurological disease or an oxidative stress-mediated cell death suppressant, it can be formulated together with a pharmaceutically acceptable carrier into a pharmaceutical composition for parenteral administration such as an injection and transrectal administration, for oral administration such as solid or liquid form, or the like.

As the form of a composition for injection, a pharmaceutically acceptable aseptic water, a non-aqueous solution, a suspension solution or an emulsion is mentioned. Examples of a non-aqueous carrier, diluent, solvent or vehicle include propylene glycol, polyethylene glycol, a vegetable oil such as olive oil and an injectable organic ester such as ethyl oleate. Furthermore, the composition may contain additives such as an antiseptic agent, a moisturizing agent, an emulsifier and a dispersant. Such a composition can be sterilized, for example, by filtration with a bacterial-retaining filter or by adding a sterilizing agent in the form of an aseptic solid composition, which is capable of being dissolved in sterilized water or a small amount of another sterilized injectable medium, immediately before use.

As a solid preparation for oral administration, capsules, tablets, pills, powders, grains and others are mentioned. A solid preparation is prepared generally by mixing the acylaminoimidazole derivative or a salt thereof as mentioned above with at least one type of inert diluent such as sucrose, lactose and starch. To the preparation, additional substances other than the inert diluent, such as a lubricant (for example, a coating agent such as magnesium stearate) can be added in a general process for producing the preparation. In the cases of capsules, tablets and pills, a buffer can be added. To tablets and pills, an enteric film can be applied.

Examples of a liquid preparation for oral administration include an inert diluent usually used by those skilled in the art, e.g., water-containing pharmaceutically acceptable emulsion, a solution, a suspension solution, a syrup agent and an elixir agent. In addition to the inert diluent, additives such as a moisturizing agent, an emulsifier, a thickener, a sweetener, a seasoning agent and a flavoring agent can be blended with the composition. In the case of a preparation for transrectal administration, an excipient such as cacao butter and suppository wax is preferably added in addition to the acylaminoimidazole derivative or a salt thereof as mentioned above.

In the case where the pharmaceutical composition of the present invention is used as an agent for preventing or treating neurological disease or an oxidative stress-mediated cell death suppressant, the use amount of acylaminoimidazole derivative of the present invention or a salt thereof varies depending upon symptom, age, body weight, relative health condition, the presence of other medication, route of administration and others. In the case of oral agent, an effective amount thereof generally for e.g., a patient (warm-blooded animal, particularly a human) as an active ingredient per day per kg of body weight is preferably 0.1 to 1000 mg, more preferably 1 to 300 mg. The use amount for an adult patient of normal body weight per day preferably falls within the range of 10 to 800 mg. In the case of a parenteral agent, use amount per kg of body weight per day is preferably 0.1 to 1000 mg, more preferably 10 to 800 mg. This is desirably administered once a day or several times by dividing the dosage in accordance with the symptom.

EXAMPLES

The present invention will be described in detail based on Examples; however, the present invention is not limited to these Examples.

Synthesis Example 1

Synthesis Of tert-butyl imino{[(mesityloxy)acetyl]amino}methylcarbamate

Mesityloxyacetic acid (89.3 g; 460 mmol), diisopropylethylamine (297.1 g; 2.3 mol), tert-butyl amino(imino)methylcarbamate (76.8 g; 480 mmol), and 1-hydroxybenzotriazole monohydrate (62.4 g; 460 mmol) were dissolved in N,N-dimethylformamide (1.0 L), 2-(1H)-benzotriazol-1-yl-1,1,3,3-tetramethyluronium hexafluorophosphate (183.1 g; 460 mmol) was added thereto, and the mixture was stirred for 25 hours at room temperature. The precipitated crystals were collected by filtration, washed with ethyl acetate and then dried to give 135.2 g of the title compound (yield 88%).

$^1$H-NMR (CDCl$_3$) δ:
1.51 (9H, s), 2.21 (6H, s), 2.24 (3H, s), 4.31 (2H, s), 6.83 (2H, s)

Synthesis Example 2

Synthesis of N-[amino(imino)methyl]-2-(mesityloxy)acetamide

To tert-butyl imino{[(mesityloxy)acetyl]amino}methylcarbamate (152.0 g; 450 mmol) obtained in Synthesis Example 1, anisole (5.0 mL) and trifluoroacetic acid (150 mL) were added, and the mixture was stirred for 2 hours at 60° C. To the reaction solution, chloroform (3.0 L) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 82.6 g of the title compound (yield 78%).

$^1$H-NMR (d$_6$-DMSO) δ:
2.16 (9H, s), 4.10 (2H, s), 6.79 (2H, s)

Synthesis Example 3

Synthesis of tert-butyl imino{[(2,6-dimethylphenoxy)acetyl]amino}methylcarbamate (2,6-Dimethylphenoxy)acetic acid (5.41 g; 30 mmol), diisopropylethylamine (19.39 g; 150 mmol), tert-butyl amino(imino)methylcarbamate (5.73 g; 36 mmol), and 1-hydroxybenzotriazole monohydrate (5.52 g; 36 mmol) were dissolved in N,N-dimethylformamide (120 mL), 2-(1H)-benzotriazol-1-yl-1,1,3,3-tetramethyluronium hexafluorophosphate (13.66 g; 36 mmol) was added thereto, and the mixture was stirred for 65 hours at room temperature. To the reaction solution, ethyl acetate (400 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure. The resulting crystals were dispersed in diethyl ether, collected by filtration and dried to give 9.03 g of the title compound (yield 94%).

$^1$H-NMR (CDCl$_3$) δ:
1.51 (9H, s), 2.25 (6H, s), 4.35 (2H, s), 6.97-6.99 (1H, m), 7.02-7.03 (2H, m)

Synthesis Example 4

Synthesis of N-[amino(imino)methyl]-2-(2,6-dimethylphenoxy)acetamide

To tert-butyl imino{[(2,6-dimethylphenoxy)acetyl]amino}methylcarbamate (9.03 g; 28 mmol) obtained in Synthesis Example 3, anisole (0.2 mL) and trifluoroacetic acid (20 mL) were added, and the mixture was stirred for 3 hours at 60° C. To the reaction solution, chloroform (300 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 4.45 g of the title compound (yield 72%).

$^1$H-NMR (d$_6$-DMSO) δ:
2.20 (6H, s), 4.14 (2H, s), 6.88 (1H, t, J=7.6 Hz), 6.99 (2H, d, J=6.9 Hz)

Synthesis Example 5

Synthesis of tert-butyl imino{([2-(mesityloxy)propanoyl]amino}methylcarbamate 2-(Mesityloxy)propionic acid (11.4 g; 50 mmol), diisopropylethylamine (32.3 g; 250 mmol), tert-butyl amino(imino)methylcarbamate (9.55 g; 60 mmol), and 1-hydroxybenzotriazole monohydrate (9.19 g; 60 mmol) were dissolved in N,N-dimethylformamide (200 mL), 2-(1H)-benzotriazol-1-yl-1,1,3,3-tetramethyluronium hexafluorophosphate (22.8 g; 60 mmol) was added, and the mixture was stirred for 24 hours at room temperature. To the reaction solution, ethyl acetate (500 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure. The resulting crystals were dispersed in diethyl ether, collected by filtration and dried to give 9.78 g of the title compound (yield 56%).

$^1$H-NMR (CDCl$_3$) δ:
1.43 (3H, d, J=6.9 Hz), 1.49 (9H, s), 2.18 (6H, s), 2.24 (3H, s), 4.45 (1H, q, J=6.9 Hz), 6.82 (2H, s), 8.88 (2H, br), 9.06 (1H, br)

Synthesis Example 6

Synthesis of N-[amino(imino)methyl]-2-(mesityloxy)propanamide

To tert-butyl imino{[2-(mesityloxy)propanoyl]amino}methylcarbamate (9.70 g; 28 mmol) obtained in Synthesis Example 5, anisole (0.2 mL) and trifluoroacetic acid (20 mL) were added, and the mixture was stirred for 2 hours at 60° C. To the reaction solution was added chloroform (300 mL), and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 7.10 g of the title compound (yield 100%).

¹H-NMR (d₆-DMSO) δ:
1.33 (3H, d, J=6.9 Hz), 2.15 (9H, s), 4.11 (1H, q, J=6.9 Hz), 6.75 (2H, s)

Synthesis Example 7

Synthesis of tert-butyl imino{[(2R)-2-(mesityloxy)propanoyl]amino}methylcarbamate (2R)-2-(Mesityloxy)propionic acid (11.6 g; 55 mmol), diisopropylethylamine (35.6 g; 275 mmol), tert-butyl amino(imino)methylcarbamate (8.8 g; 55 mmol), and 1-hydroxybenzotriazole monohydrate (8.4 g; 55 mmol) were dissolved in N,N-dimethylformamide (150 mL), 2-(1H)-benzotriazol-1-yl-1,1,3,3-tetramethyluronium hexafluorophosphate (20.9 g; 55 mmol) was added thereto, and the mixture was stirred for 18 hours at room temperature. To the reaction solution, ethyl acetate (400 mL) was added, and the mixture was washed sequentially with 10% aqueous citric acid solution, brine, and saturated aqueous sodium bicarbonate solution. The organic layer was dried over anhydrous magnesium sulfate and then distilled under reduced pressure. The resulting oily substance was crystallized from diisopropyl ether, collected by filtration and dried to give 14.1 g of the title compound (yield 73%).
¹H-NMR (CDCl₃) δ:
1.43 (3H, d, J=6.9 Hz), 1.50 (9H, s), 2.18 (6H, s), 2.24 (3H, s), 4.45 (1H, q, J=6.9 Hz), 6.82 (2H, s)

Synthesis Example 8

Synthesis of N-[amino(imino)methyl]-(2R)-2-(mesityloxy)propanamide

To tert-butyl imino{[(2R)-2-(mesityloxy)propanoyl]amino}methylcarbamate (13.98 g; 40 mmol) obtained in Synthesis Example 7, anisole (2.0 mL) and trifluoroacetic acid (20 mL) were added, and the mixture was stirred for 2 hours at 60° C. To the reaction solution, chloroform (400 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 8.85 g of the title compound (yield 88%).
¹H-NMR (d₆-DMSO) δ:
1.33 (3H, d, J=6.4 Hz), 2.15 (9H, s), 4.11 (1H, q, J=6.4 Hz), 6.75 (2H, s)

Synthesis Example 9

Synthesis of tert-butyl imino{[(2S)-2-(mesityloxy)propanoyl]amino}methylcarbamate (2S)-2-(Mesityloxy)propionic acid (5.6 g; 27 mmol), diisopropylethylamine (17.3 g; 133 mmol), tert-butyl amino(imino)methylcarbamate (4.3 g; 27 mmol), and 1-hydroxybenzotriazole monohydrate (4.1 g; 27 mmol) were dissolved in N,N-dimethylformamide (80 mL), 2-(1H)-benzotriazol-1-yl-1,1,3,3-tetramethyluronium hexafluorophosphate (10.2 g; 27 mmol) was added, and the mixture was stirred for 137 hours at room temperature. To the reaction solution, ethyl acetate (400 mL) was added, and the mixture was washed sequentially with 10% aqueous citric acid solution, brine, and saturated aqueous sodium bicarbonate solution. The organic layer was dried over anhydrous magnesium sulfate and then distilled under reduced pressure, to give 8.6 g of the title compound (yield 91%) as an oil.
¹H-NMR (CDCl₃) δ:
1.43 (3H, d, J=6.9 Hz), 1.50 (9H, s), 2.18 (6H, s), 2.24 (3H, s), 4.46 (1H, q, J=6.9 Hz), 6.82 (2H, s)

Synthesis Example 10

Synthesis of N-[amino(imino)methyl]-(2S)-2-(mesityloxy)propanamide

To tert-butyl imino{[(2S)-2-(mesityloxy)propanoyl]amino}methylcarbamate (8.6 g; 25 mmol) obtained in Synthesis Example 9, anisole (1.0 mL) and trifluoroacetic acid (10 mL) were added, and the mixture was stirred for 1 hour at 60° C. To the reaction solution, chloroform (400 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 3.0 g of the title compound (yield 49%).
¹H-NMR (d₆-DMSO) δ:
1.33 (3H, d, J=6.6 Hz), 2.15 (9H, s), 4.11 (1H, q, J=6.6 Hz), 6.75 (2H, s)

Synthesis Example 11

Synthesis of tert-butyl imino{[2-(mesityloxy)-2-methylpropanoyl]amino}methylcarbamate 2-(Mesityloxy)-2-methylpropionic acid (4.45 g; 20 mmol), diisopropylethylamine (12.93 g; 100 mmol), tert-butyl amino(imino)methylcarbamate (3.82 g; 24 mmol), and 1-hydroxybenzotriazole monohydrate (3.68 g; 24 mmol) were dissolved in N,N-dimethylformamide (100 mL), 2-(1H)-benzotriazol-1-yl-1,1,3,3-tetramethyluronium hexafluorophosphate (9.10 g; 24 mmol) was added, and the mixture was stirred for 41 hours at room temperature. To the reaction solution, ethyl acetate (300 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure. The resulting crystals were dispersed in diisopropyl ether, collected by filtration and dried to give 4.82 g of the title compound (yield 66%).
¹H-NMR (CDCl₃) δ:
1.43 (6H, s), 1.50 (9H, s), 2.14 (6H, s), 2.23 (3H, s), 6.78 (2H, s)

Synthesis Example 12

Synthesis of N-[amino(imino)methyl]-2-(mesityloxy)-2-methylpropanamide

To tert-butyl imino{[2-(mesityloxy)-2-methylpropanoyl]amino}methylcarbamate (4.72 g; 13 mmol) obtained in Synthesis Example 11, anisole (1.0 mL) and trifluoroacetic acid (13 mL) were added, and the mixture was stirred for 2 hours at 60° C. To the reaction solution, chloroform (300 mL) was added, and the mixture was washed with 10% aqueous sodium hydroxide solution. The organic layer was dried over anhydrous magnesium sulfate and then distilled under reduced pressure, and the resulting crystals were dispersed in diisopropyl ether, collected by filtration and dried to give 2.82 g of the title compound (yield 82%).
¹H-NMR (CDCl₃) δ:
1.41 (6H, s), 2.16 (6H, s), 2.22 (3H, s), 6.76 (2H, s)

Synthesis Example 13

Synthesis of tert-butyl imino{[(mesitylthio)acetyl]amino}methylcarbamate

Mesitylthio acetic acid (6.90 g; 33 mmol), diisopropylethylamine (21.2 g; 164 mmol), tert-butyl amino(imino)methylcarbamate (6.37 g; 40 mmol), and 1-hydroxybenzotriazole monohydrate (6.13 g; 40 mmol) were dissolved in N,N-dimethylformamide (120 mL), 2-(1H)-benzotriazol-1-yl-1,1,3,3-tetramethyluronium hexafluorophosphate (15.2 g; 40 mmol) was added, and the mixture was stirred for 15 hours at room temperature. To the reaction solution, ethyl acetate (300 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure to give 14.3 g of the title compound (yield 100%) as an oil.

$^1$H-NMR (CDCl$_3$) δ:
1.48 (9H, s), 2.25 (3H, s), 2.49 (6H, s), 3.36 (2H, s), 6.92 (2H, s)

Synthesis Example 14

Synthesis of N-[amino(imino)methyl]-2-(mesitylthio)acetamide

To tert-butyl imino{[(mesitylthio)acetyl]amino}methylcarbamate (14.3 g; equivalent to 33 mmol) obtained in Synthesis Example 13, anisole (1.0 mL) and trifluoroacetic acid (15 mL) were added, and the mixture was stirred for 1 hour at 60° C. To the reaction solution, chloroform (200 mL) was added, and the mixture was washed with 10% aqueous sodium hydroxide solution. The organic layer was dried over anhydrous magnesium sulfate and then distilled under reduced pressure, and the resulting crystals were dispersed in ethyl acetate/diethyl ether, collected by filtration and dried to give 6.72 g of the title compound (yield 82%).

$^1$H-NMR (d$_6$-DMSO) δ:
2.20 (3H, s), 2.42 (6H, s), 3.17 (2H, s), 6.92 (2H, s)

Synthesis Example 15

Synthesis of tert-butyl({[mesityl(methyl)amino]acetyl}amino)(imino)methylcarbamate

[Mesityl(methyl)amino]acetic acid (6.67 g; 32 mmol), diisopropylethylamine (20.68 g; 160 mmol), tert-butyl amino(imino)methylcarbamate (6.11 g; 38 mmol), and 1-hydroxybenzotriazole monohydrate (5.88 g; 38 mmol) were dissolved in N,N-dimethylformamide (150 mL), 2-(1H)-benzotriazol-1-yl-1,1,3,3-tetramethyluronium hexafluorophosphate (14.56 g; 38 mmol) was added thereto, and the mixture was stirred for 65 hours at room temperature. To the reaction solution, ethyl acetate (400 mL) was added, and the mixture was washed with 10% aqueous citric acid solution, brine, and saturated aqueous sodium bicarbonate solution. The organic layer was dried over anhydrous magnesium sulfate and then distilled under reduced pressure. The resulting crystals were dispersed in diethyl ether, collected by filtration and dried to give 5.82 g of the title compound (yield 52%).

$^1$H-NMR (CDCl$_3$) δ:
1.52 (9H, s), 2.24 (3H, s), 2.37 (6H, s), 2.77 (3H, s), 3.77 (2H, s), 6.84 (2H, s)

Synthesis Example 16

Synthesis of N-[amino(imino)methyl]-2-[mesityl(methyl)amino]acetamide

To tert-butyl({[mesityl(methyl)amino]acetyl}amino)(imino)methylcarbamate (5.82 g; 17 mmol) obtained in Synthesis Example 15, anisole (1.0 mL) and trifluoroacetic acid (10 mL) were added, and the mixture was stirred for 2 hours at 60° C. To the reaction solution, chloroform (200 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 2.91 g of the title compound (yield 70%).

$^1$H-NMR (CDCl$_3$) δ:
2.23 (3H, s), 2.33 (6H, s), 2.82 (3H, s), 3.70 (2H, s), 6.82 (2H, s)

Synthesis Example 17

Synthesis of tert-butyl imino[(3-mesitylpropanoyl)amino]methylcarbamate

3-Mesitylpropionic acid (4.40 g; 23 mmol), diisopropylethylamine (14.8 g; 115 mmol), tert-butyl amino(imino)methylcarbamate (4.40 g; 28 mmol), and 1-hydroxybenzotriazole monohydrate (4.22 g; 28 mmol) were dissolved in N,N-dimethylformamide (92 mL), 2-(1H)-benzotriazol-1-yl-1,1,3,3-tetramethyluronium hexafluorophosphate (10.5 g; 28 mmol) was added thereto, and the mixture was stirred for 17 hours at room temperature. To the reaction solution, ethyl acetate (300 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure. The resulting oily substance was crystallized from diethyl ether/diisopropyl ether, collected by filtration and dried to give 7.10 g of the title compound (yield 93%).

$^1$H-NMR (CDCl$_3$) δ:
1.47 (9H, s), 2.24 (3H, s), 2.28 (6H, s), 2.43-2.47 (2H, m), 2.93-2.97 (2H, m), 6.84 (2H, s)

Synthesis Example 18

Synthesis of N-[amino(imino)methyl]-3-mesitylpropanamide

To tert-butyl imino[(3-mesitylpropanoyl)amino]methylcarbamate (7.10 g; 21 mmol) obtained in Synthesis Example 17, anisole (2 mL) and trifluoroacetic acid (25 mL) were added, and the mixture was stirred for 1 hour at 60° C. To the reaction solution, chloroform (400 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 4.51 g of the title compound (yield 91%).

$^1$H-NMR (d$_6$-DMSO) δ:
2.16 (3H, s), 2.16-2.19 (2H, m), 2.22 (6H, s), 2.73-2.77 (2H, m), 6.76 (2H, s)

Synthesis Example 19

Synthesis of tert-butyl imino{[(2E)-3-mesityl-2-propenoyl]amino}methylcarbamate (2E)-3-Mesitylacrylic acid (8.0 g; 42 mmol), diisopropylethylamine (27.2 g; 210 mmol), tert-butyl amino(imino)methylcarbamate (8.03 g; 50 mmol), and 1-hydroxybenzotriazole monohydrate (7.73 g; 50 mmol) were dissolved in N,N-dimethylformamide (170 mL), 2-(1H)-benzotriazol-1-yl-1,1,3,3-tetramethyluronium hexafluorophosphate (19.2 g; 50 mmol) was added thereto, and the mixture was stirred for 20 hours at room temperature. To the reaction solution, ethyl acetate (500 mL) was added, and the mixture was washed with 10% aqueous citric acid solution, brine, saturated aqueous sodium bicarbonate solution, and then brine. The organic layer was dried over anhydrous magnesium sulfate and then distilled under reduced pressure, to give 13.9 g of the title compound (yield 100%) as an oil.

$^1$H-NMR (CDCl$_3$) δ:
1.44 (9H, s), 2.28 (3H, s), 2.32 (6H, s), 6.14 (1H, d, J=16.0 Hz), 6.88 (2H, s), 7.89 (1H, d, J=16.0 Hz)

Synthesis Example 20

Synthesis of (2E)-N-[amino(imino)methyl]-3-mesitylacrylamide

To tert-butyl imino{[(2E)-3-mesityl-2-propenoyl]amino}methylcarbamate (13.9 g; equivalent to 42 mmol) obtained in Synthesis Example 19, anisole (2 mL) and trifluoroacetic acid (30 mL) were added, and the mixture was stirred for 2 hours at 60° C. To the reaction solution, chloroform (300 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 9.1 g of the title compound (yield 94%).

$^1$H-NMR (d$_6$-DMSO) δ:
2.22 (3H, s), 2.24 (6H, s), 6.03 (1H, d, J=16.0 Hz), 6.88 (2H, s), 7.50 (1H, d, J=16.0 Hz)

Synthesis Example 21

Synthesis of tert-butyl{[(mesityloxy)acetyl]imino}(methylamino)methylcarbamate (Mesityloxy)acetic acid (7.77 g; 40 mmol), diisopropylethylamine (25.9 g; 200 mmol), tert-butyl imino(methylamino)methylcarbamate (7.08 g; 41 mmol), and 1-hydroxybenzotriazole monohydrate (7.35 g; 48 mmol) were dissolved in N,N-dimethylformamide (200 mL), 2-(1H)-benzotriazol-1-yl-1,1,3,3-tetramethyluronium hexafluorophosphate (18.2 g; 48 mmol) was added thereto, and the mixture was stirred for 17 hours at room temperature. To the reaction solution, ethyl acetate (400 mL) was added, and the mixture was washed with 10% aqueous citric acid solution, brine, and saturated aqueous sodium bicarbonate solution. The organic layer was dried over anhydrous magnesium sulfate and then distilled under reduced pressure to give 12.2 g of the title compound (yield 87%) as an oil.

$^1$H-NMR (CDCl$_3$) δ:
1.49 (9H, s), 2.26 (6H, s), 2.28 (3H, s), 3.02 (3H, d, J=5.0 Hz), 4.37 (2H, s), 6.85 (2H, s)

Synthesis Example 22

Synthesis of N-[imino(methylamino)methyl]-2-(mesityloxy)acetamide

To tert-butyl{[(mesityloxy)acetyl]imino}(methylamino)methylcarbamate (12.2 g; 35 mmol) obtained in Synthesis Example 21, anisole (1.0 mL) and trifluoroacetic acid (35 mL) were added, and the mixture was stirred for 1 hour at 60° C. To the reaction solution, chloroform (200 mL) was added, and the mixture was washed with 10% aqueous sodium hydroxide solution. The organic layer was dried over anhydrous magnesium sulfate and then distilled under reduced pressure, and the resulting crystals were dispersed in diethyl ether, collected by filtration and dried to give 7.65 g of the title compound (yield 88%).

$^1$H-NMR (CDCl$_3$) δ:
2.23 (3H, s), 2.26 (6H, s), 2.84 (3H, s), 4.28 (2H, s), 6.81 (2H, s)

Synthesis Example 23

Synthesis of tert-butyl 4-(2-nitrophenyl)-1H-imidazol-2-ylcarbamate tert-Butyl amino(imino)methylcarbamate (4.78 g; 30 mmol) was dissolved in N,N-dimethylformamide (30 mL), 2-bromo-2'-nitroacetophenone (2.44 g; 10 mmol) was added thereto, and the mixture was stirred for 144 hours at room temperature. To the reaction solution, water (100 mL) was added, and the precipitated powder was collected by filtration. The resulting powder was dissolved in ethyl acetate (200 mL), and the mixture was washed with saturated aqueous sodium bicarbonate solution (two times). The organic layer was dried over anhydrous magnesium sulfate and then distilled under reduced pressure. The resulting residue was dispersed in acetone/diethyl ether, collected by filtration and dried to give 1.09 g of the title compound (yield 36%).

$^1$H-NMR (CDCl$_3$) δ:
1.62 (9H, s), 5.61 (2H, s), 7.06 (1H, s), 7.37-7.40 (1H, m), 7.53 (1H, dt, J=1.4 Hz, 7.8 Hz), 7.65 (1H, dd, J=1.1 Hz, 8.0 Hz), 7.75 (1H, dd, J=1.4 Hz, 7.8 Hz)

Synthesis Example 24

Synthesis of 2-amino-4-(2-nitrophenyl)-1H-imidazole dihydrochloride tert-Butyl 4-(2-nitrophenyl)-1H-imidazol-2-ylcarbamate (2.75 g; 9.0 mmol) obtained in Synthesis Example 23 was dissolved in 4 mol/L hydrochloric acid/1,4-dioxane (40 mL) and the mixture was stirred for 2 hours at 70° C. The solvent was distilled off under reduced pressure and the resulting crystals were dispersed in acetone, collected by filtration and dried to give 2.0 g of the title compound (yield 80%).

$^1$H-NMR (d$_6$-DMSO) δ:
7.13 (1H, s), 7.66 (2H, s), 7.68-7.73 (2H, m), 7.83 (1H, dt, J=1.2 Hz, 7.6 Hz), 8.14 (1H, dd, J=0.9 Hz, 8.2 Hz)

Synthesis Example 25

Synthesis of tert-butyl 4-pyridin-2-yl-1H-imidazol-2-ylcarbamate tert-Butyl amino(imino)methylcarbamate (33.4 g; 210 mmol) was dissolved in N,N-dimethylformamide (300 mL), 2-bromo-1-pyridin-2-ylethanone (17.4 g; 87 mmol) was added thereto, and the mixture was stirred for 143 hours at room temperature. To the reaction solution, ethyl acetate (2.0 L) was added, and the mixture was washed with saturated aqueous sodium bicarbonate solution (three times). The organic layer was dried over anhydrous magnesium sulfate and then distilled under reduced pressure. The resulting oily substance was crystallized from diethyl ether and the resulting crystals were collected by filtration and dried to give 6.2 g of the title compound (yield 27%).

$^1$H-NMR (d$_6$-DMSO) δ:
1.48 (9H, s), 7.15 (1H, t, J=5.3 Hz), 7.34 (1H, s), 7.70-7.76 (2H, m), 8.46 (1H, d, J=4.1 Hz), 10.38 (1H, br), 11.60 (1H, br)

Synthesis Example 26

Synthesis of 2-amino-4-(pyridine-2-yl)-1H-imidazole trihydrochloride

To tert-Butyl 4-pyridin-2-yl-1H-imidazol-2-ylcarbamate (1.90 g; 7.3 mmol) obtained in Synthesis Example 25, 10% hydrochloric acid/methanol solution (30 mL) was added, and the mixture was heated under reflux for 4 hours. The solvent was distilled under reduced pressure and the resulting crystals were dispersed in ethanol, collected by filtration and dried to give 1.55 g of the title compound (yield 79%).

$^1$H-NMR (d$_6$-DMSO) δ:
7.39-7.41 (1H, m), 7.76 (1H, s), 7.91-7.98 (2H, m), 8.60-8.61 (1H, m)

Synthesis Example 27

Synthesis of 2-(pyridin-2-yl)imidazo[1,2-a]pyrimidine hydrobromide

2-Bromo-1-pyridin-2-ylethanone (66.1 g; 330 mmol) was dissolved in ethanol (330 mL), 2-aminopyrimidine (31.5 g; 330 mmol) was added thereto, and the mixture was stirred for 17 hours at 70° C. The precipitated crystals were collected by filtration, washed with acetone, and then dried to give 70.7 g of the title compound (yield 77%).

$^1$H-NMR (d$_6$-DMSO) δ:
7.43 (1H, dd, J=4.2 Hz, 6.7 Hz), 7.63-7.66 (1H, m), 8.21 (1H, dt, J=1.6 Hz, 7.9 Hz), 8.33 (1H, d, J=8.0 Hz), 8.76-8.78 (1H, m), 8.83 (1H, s), 8.86 (1H, dd, J=1.8 Hz, 4.2 Hz), 9.23 (1H, dd, J=2.0 Hz, 6.9 Hz)
Mass: M+1=197.05

Synthesis Example 28

Synthesis of 2-(pyridin-2-yl)imidazo[1,2-a]pyrimidine

2-Pyridin-2-ylimidazo[1,2-a]pyrimidine hydrobromide (73.9 g; 267 mmol) obtained in Synthesis Example 27 was suspended in chloroform (800 mL) and methanol (200 mL). Water (200 mL) was added to make homogeneous solution. Saturated aqueous sodium bicarbonate solution was added thereto to make it alkaline, and the solution was separated. The aqueous layer was further extracted with chloroform (400 mL). The organic layers were combined, dried over anhydrous magnesium sulfate, and then distilled under reduced pressure. The resulting crystals were dispersed in acetone, collected by filtration and dried to give 48.0 g of the title compound (yield 92%).

$^1$H-NMR (d$_6$-DMSO) δ:
7.10 (1H, dd, J=4.2 Hz, 6.8 Hz), 7.37 (1H, ddd, J=1.3 Hz, 4.8 Hz, 7.5 Hz), 7.92 (1H, dt, J=1.9 Hz, 7.8 Hz), 8.15 (1H, dt, J=1.1 Hz, 7.8 Hz), 8.45 (1H, s), 8.58 (1H, dd, J=2.0 Hz, 4.2 Hz), 8.63-8.64 (1H, m), 9.01 (1H, dd, J=2.0 Hz, 6.7 Hz)
Mass: M+1=197.07

Synthesis Example 29

Synthesis of 2-amino-4-(pyridin-2-yl)-1H-imidazole trihydrochloride

2-Pyridin-2-ylimidazo[1,2-a]pyrimidine (50.0 g; 255 mmol) obtained in Synthesis Example 28 was suspended in ethanol (900 mL), hydrazine monohydrate (50.0 g; 1.0 mol) was added thereto, and the mixture was heated under reflux for 15 hours. The solvent was distilled off under reduced pressure and azeotroped with water (300 mL) (three times), and ethanol (300 mL). The residue was dissolved in 2 mol/L aqueous hydrochloric acid solution and washed with ethyl acetate. The aqueous layer was distilled under reduced pressure, and the resulting crystals were dispersed in ethanol, collected by filtration and dried to give 63.5 g of the title compound (yield 92%).

$^1$H-nmr (d$_6$-DMSO) δ:
7.39 (1H, ddd, J=1.4 Hz, 5.1 Hz, 7.2 Hz), 7.58 (2H, brs), 7.74 (1H, s), 7.91 (1H, dt, J=1.2 Hz, 8.0 Hz), 7.95 (1H, ddd, J=1.7 Hz, 7.4 Hz, 8.0 Hz), 8.61 (1H, ddd, J=1.0 Hz, 1.7 Hz, 4.9 Hz), 12.48 (1H, br)
Mass: M+1=161.02

Comparative Example 1

Preparation of 2-(mesityloxy)-N-[4-(pyridin-2-yl)-1H-imidazol-2-yl]acetamide (Compound 1e)

N-[Amino(imino)methyl]-2-(mesityloxy)acetamide (4.23 g; 18 mmol) obtained in Synthesis Example 2 was dissolved in N,N-dimethylformamide (40 mL), 2-bromo-1-pyridin-2-ylethanone (1.20 g; 6.0 mmol) was added thereto, and the mixture was stirred for 46 hours at room temperature. To the reaction solution, ethyl acetate (200 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (2 to 4% methanol/chloroform), and the crystals were dispersed in ethyl acetate, collected by filtration and dried to give 270 mg of the title compound (yield 13%) represented by the above formula (Ie).

$^1$H-NMR (d$_6$-DMSO) δ:
2.19 (3H, s), 2.23 (6H, s), 4.45 (2H, s), 6.84 (2H, s), 7.17-7.19 (1H, m), 7.42 (1H, s), 7.74-7.79 (2H, m), 8.49 (1H, d, J=4.6 Hz), 11.35 (1H, br), 11.93 (1H, br)
Mass: M+1=337.34

Example 1

Preparation of 2-(mesityloxy)-N-[4-(2-benzyloxyphenyl)-1H-imidazol-2-yl]acetamide (Compound 1)

N-[Amino(imino)methyl]-2-(mesityloxy)acetamide (7.06 g, 30 mmol) obtained in Synthesis Example 2 was dissolved in N,N-dimethylformamide (100 mL), 2-bromo-2'-(benzyloxy)acetophenone (3.05 g; 10 mmol) was added thereto, and the mixture was stirred for 96 hours at room temperature. To the reaction solution was added ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 3% methanol/chloroform), and the resulting oily substance was crystallized from diethyl ether to give 650 mg of the title compound (yield 15%) expressed by the following formula (Ex. 1).

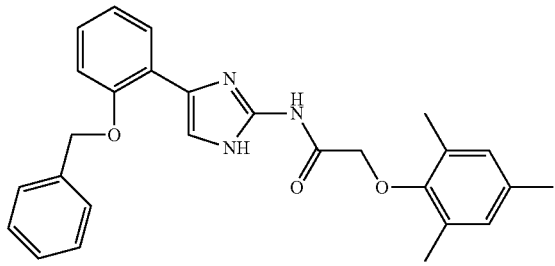

(Ex. 1)

$^1$H-NMR (d$_6$-DMSO) δ:
2.19 (3H, s), 2.22 (6H, s), 4.42 (2H, s), 5.25 (2H, s), 6.83 (2H, s), 6.95-6.99 (1H, m), 7.12-7.17 (2H, m), 7.27 (1H, s), 7.35-7.38 (1H, m), 7.41-7.44 (2H, m), 7.51-7.52 (2H, m), 7.99 (1H, s), 11.20 (1H, s), 11.73 (1H, s)
Mass: M+1=442.36

Example 2

Preparation of N-[4-(2-hydroxyphenyl)-1H-imidazol-2-yl]-2-(mesityloxy)acetamide (Compound 2)

To 2-(mesityloxy)-N-[4-(2-benzyloxyphenyl)-1H-imidazol-2-yl]acetamide (Compound 1) (530 mg; 1.2 mmol) obtained in Example 1, 25% hydrobromic acid/acetic acid solution (8.0 mL) was added, and the mixture was stirred for 1 hour at 60° C. To the reaction solution, chloroform (100 mL) was added, and the mixture was washed with saturated aqueous sodium bicarbonate solution. The organic layer was dried over anhydrous magnesium sulfate, and then distilled under reduced pressure. The resulting crystals were dispersed in diethyl ether, collected by filtration and dried to give 180 mg of the title compound (yield 43%) expressed by the following formula (Ex. 2).

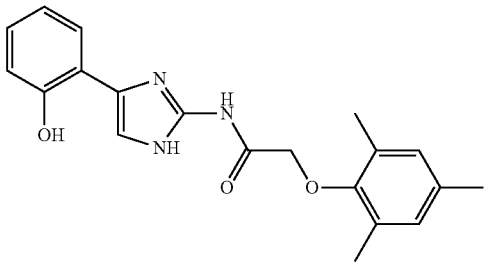

(Ex. 2)

$^1$H-NMR (d$_6$-DMSO) δ:
2.20 (3H, s), 2.23 (6H, s), 4.46 (2H, s), 6.78-6.83 (2H, m), 6.85 (2H, s), 7.03-7.06 (1H, m), 7.39 (1H, s), 7.68 (1H, dd, J=1.4 Hz, 7.8 Hz)
Mass: M+1=352.24

Example 3

Preparation of 2-(mesityloxy)-N-[4-(3-methoxyphenyl)-1H-imidazol-2-yl]acetamide (Compound 3)

N-[Amino(imino)methyl]-2-(mesityloxy)acetamide (3.53 g; 15 mmol) obtained in Synthesis Example 2 was dissolved in N,N-dimethylformamide (25 mL), 2-bromo-3'-methoxyacetophenone (1.20 g; 5.0 mmol) was added thereto, and the mixture was stirred for 70 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 3% methanol/chloroform), and the resulting crystals were dispersed in ethyl acetate, collected by filtration and dried to give 140 mg of the title compound (yield 8%) expressed by the following formula (Ex. 3).

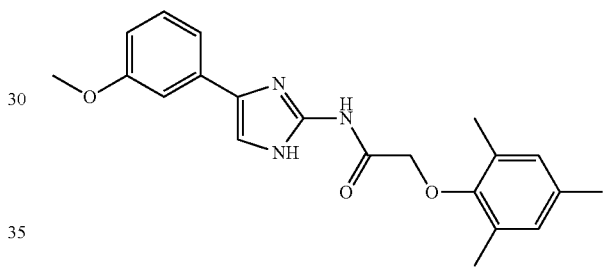

(Ex. 3)

$^1$H-NMR (d$_6$-DMSO) δ:
2.19 (3H, s), 2.23 (6H, s), 3.77 (3H, s), 4.43 (2H, s), 6.73-6.75 (1H, m), 6.84 (2H, s), 7.23 (1H, t, J=7.8 Hz), 7.30-7.31 (2H, m), 7.35 (1H, s), 11.27 (1H, br), 11.85 (1H, br)
Mass: M+1=366.41

Example 4

Preparation of 2-(mesityloxy)-N-[4-(4-methylphenyl)-1H-imidazol-2-yl]acetamide (Compound 4)

N-[Amino(imino)methyl]-2-(mesityloxy)acetamide (3.53 g; 15 mmol) obtained in Synthesis Example 2 was dissolved in N,N-dimethylformamide (25 mL), 2-bromo-4'-methylacetophenone (1.07 g; 5.0 mmol) was added thereto, and the mixture was stirred for 96 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 3% methanol/chloroform), and the resulting crystals were dispersed in ethyl acetate, collected by filtration and dried to give 100 mg of the title compound (yield 6%) expressed by the following formula (Ex. 4).

(Ex. 4)

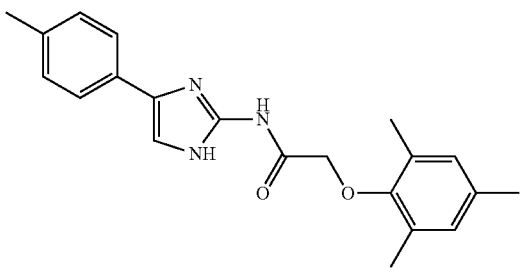

¹H-NMR (d₆-DMSO) δ:
2.19 (3H, s), 2.23 (6H, s), 2.28 (3H, s), 4.42 (2H, s), 6.84 (2H, s), 7.14 (2H, d, J=7.8 Hz), 7.25 (1H, s), 7.61 (2H, d, J=7.8 Hz), 11.21 (1H, br), 11.78 (1H, br)
Mass: M+1=350.44

Example 5

Preparation of 2-(mesityloxy)-N-[4-(1,1'-biphenyl-4-yl)-1H-imidazol-2-yl]acetamide (Compound 5)

N-[Amino(imino)methyl]-2-(mesityloxy)acetamide (3.53 g; 15 mmol) obtained in Synthesis Example 2 was dissolved in N,N-dimethylformamide (25 mL), 1-(1,1'-biphenyl-4-yl)-2-bromoethanone (1.38 g; 5.0 mmol) was added thereto, and the mixture was stirred for 52 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 4% methanol/chloroform), and the resulting crystals were dispersed in ethyl acetate, collected by filtration and dried to give 340 mg of the title compound (yield 17%) expressed by the following formula (Ex. 5).

(Ex. 5)

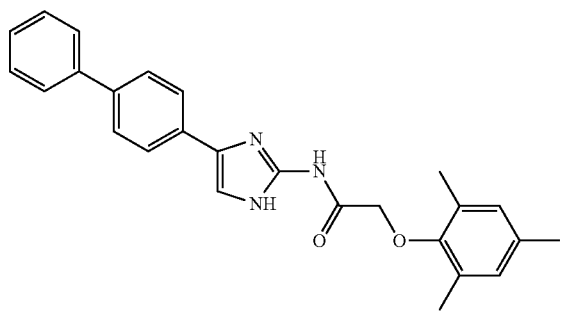

¹H-NMR (d₆-DMSO) δ:
2.20 (3H, s), 2.24 (6H, s), 4.44 (2H, s), 6.84 (2H, s), 7.35 (1H, t, J=7.4 Hz), 7.40 (1H, s), 7.46 (2H, t, J=7.7 Hz), 7.64-7.69 (4H, m), 7.82 (2H, d, J=7.8 Hz), 11.27 (1H, br), 11.89 (1H, br)
Mass: M+1=412.38

Example 6

Preparation of 2-(mesityloxy)-N-[4-(2-naphtyl)-1H-imidazol-2-yl]acetamide (Compound 6)

N-[Amino(imino)methyl]-2-(mesityloxy)acetamide (3.53 g; 15 mmol) obtained in Synthesis Example 2 was dissolved in N,N-dimethylformamide (25 mL), 2-bromo-1-(2-naphtyl)ethanone (1.25 g; 5.0 mmol) was added thereto, and the mixture was stirred for 48 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 4% methanol/chloroform), and the resulting crystals were dispersed in ethyl acetate, collected by filtration and dried to give 320 mg of the title compound (yield 17%) expressed by the following formula (Ex. 6).

(Ex. 6)

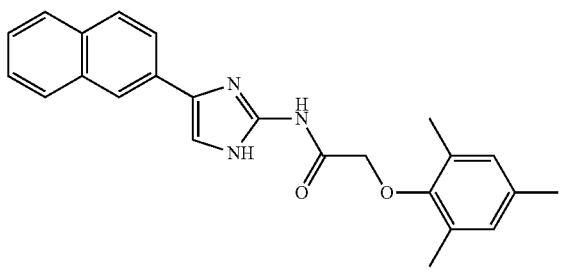

¹H-NMR (d₆-DMSO) δ:
2.20 (3H, s), 2.24 (6H, s), 4.46 (2H, s), 6.85 (2H, s), 7.43-7.49 (3H, m), 7.85-7.92 (4H, m), 8.22 (1H, s), 11.29 (1H, br), 11.92 (1H, br)
Mass: M+1=386.37

Example 7

Preparation of 2-(mesityloxy)-N-(4-phenyl-1H-imidazol-2-yl)acetamide (Compound 7)

N-[Amino(imino)methyl]-2-(mesityloxy)acetamide (3.53 g; 15 mmol) obtained in Synthesis Example 2 was dissolved in N,N-dimethylformamide (25 mL), 2-bromoacetophenone (1.0 g; 5.0 mmol) was added thereto, and the mixture was stirred for 67 hours at room temperature. To the reaction solution, ethyl acetate (200 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 3% methanol/chloroform), and the resulting crystals were dispersed in ethyl acetate/diethyl ether, collected by filtration and dried to give 280 mg of the title compound (yield 17%) expressed by the following formula (Ex. 7).

(Ex. 7)

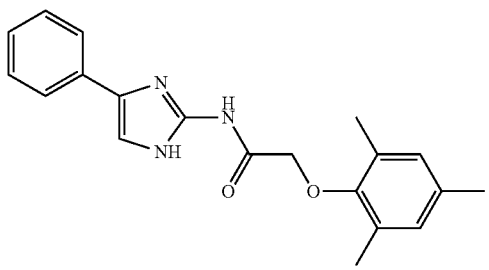

¹H-NMR (d₆-DMSO) δ:
2.19 (3H, s), 2.23 (6H, s), 4.43 (2H, s), 6.84 (2H, s), 7.17 (1H, t, J=7.3 Hz), 7.32-7.35 (3H, m), 7.72 (2H, d, J=7.3 Hz), 11.23 (1H, br), 11.83 (1H, br)
Mass: M+1=336.33

Example 8

Preparation of 2-(2,6-dimethylphenoxy)-N-[4-(pyridin-2-yl)-1H-imidazol-2-yl]acetamide (Compound 8)

N-[Amino(imino)methyl]-2-(2,6-dimethylphenoxy)acetamide (3.32 g; 15 mmol) obtained in Synthesis Example 4 was dissolved in N,N-dimethylformamide (30 mL), 2-bromo-1-pyridin-2-ylethanone (1.34 g; 5 mmol) was added thereto, and the mixture was stirred for 115 hours at room temperature. To the reaction solution, ethyl acetate (200 mL) was added, and the mixture was washed with saturated aqueous sodium bicarbonate solution (two times). The organic layer was dried over anhydrous magnesium sulfate, and then distilled under reduced pressure. The resulting residue was separated by silica gel column (0 to 4% methanol/chloroform), and crystallized from ethyl acetate to give 200 mg of the title compound (yield 12%) expressed by the following formula (Ex. 8).

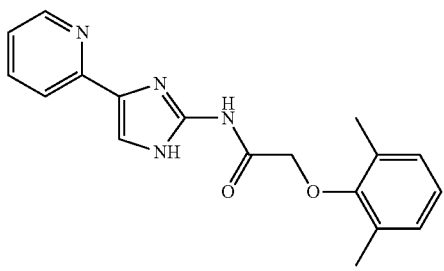

(Ex. 8)

$^1$H-NMR (d$_6$-DMSO) δ:

2.26 (6H, s), 4.48 (2H, s), 6.94 (1H, t, J=7.6 Hz), 7.03 (2H, d, J=7.6 Hz), 7.16-7.18 (1H, m), 7.40 (1H, s), 7.72-7.77 (2H, m), 8.48 (1H, d, J=4.1 Hz)

Mass: M+1=323.26

Example 9

Preparation of 2-(mesityloxy)-N-[4-(pyridin-2-yl)-1H-imidazol-2-yl]propanamide (Compound 9)

N-[Amino(imino)methyl]-2-(mesityloxy)propanamide (3.74 g; 15 mmol) obtained in Synthesis Example 6 was dissolved in N,N-dimethylformamide (50 mL), 2-bromo-1-pyridin-2-ylethanone (1.0 g; 5 mmol) was added thereto, and the mixture was stirred for 120 hours at room temperature. To the reaction solution, ethyl acetate (200 mL) was added, and the mixture was washed with saturated aqueous sodium bicarbonate solution (two times). The organic layer was dried over anhydrous magnesium sulfate, and then distilled under reduced pressure. The resulting residue was separated by silica gel column (0 to 4% methanol/chloroform), and crystallized from ethyl acetate to give 260 mg of the title compound (yield 15%) expressed by the following formula (Ex. 9).

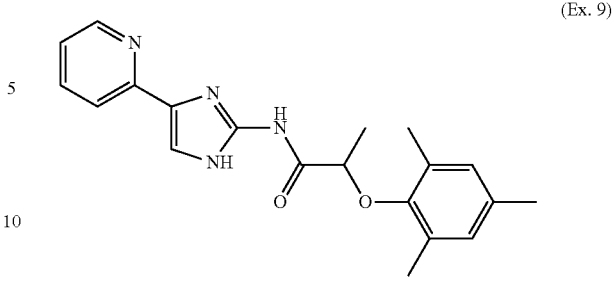

(Ex. 9)

$^1$H-NMR (d$_6$-DMSO) δ:

1.47 (3H, d, J=6.9 Hz), 2.17 (3H, s), 2.20 (6H, s), 4.59 (1H, q, J=6.9 Hz), 6.81 (2H, s), 7.17 (1H, s), 7.37 (1H, s), 7.71-7.77 (2H, m), 8.48 (1H, s), 11.36 (1H, br), 11.91 (1H, br)

Mass: M+1=351.31

Example 10

Preparation of (2R)-2-(mesityloxy)-N-[4-(pyridin-2-yl)-1H-imidazol-2-yl]propanamide (Compound 10)

N-[Amino(imino)methyl]-(2R)-2-(mesityloxy)propanamide (8.73 g; 35 mmol) obtained in Synthesis Example 8 was dissolved in N,N-dimethylformamide (30 mL), 2-bromo-1-pyridin-2-ylethanone (3.36 g; 14.2 mmol) was added thereto, and the mixture was stirred for 160 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 2% methanol/chloroform), and crystallized from diethyl ether to give 640 mg of the title compound (yield 13%) expressed by the following formula (Ex. 10).

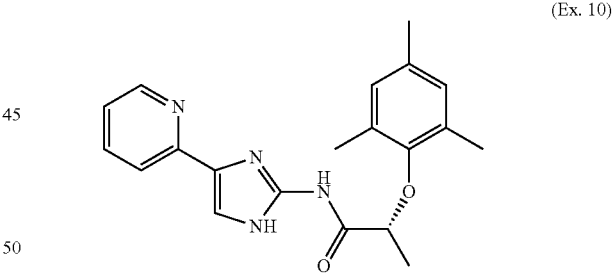

(Ex. 10)

$^1$H-NMR (d$_6$-DMSO) δ:

1.47 (3H, d, J=6.4 Hz), 2.17 (3H, s), 2.20 (6H, s), 4.59 (1H, q, J=6.4 Hz), 6.81 (2H, s), 7.17 (1H, t, J=5.7 Hz), 7.38 (1H, s), 7.71-7.77 (2H, m), 8.48 (1H, s), 11.33 (1H, br), 11.91 (1H, br)

Mass: M+1=351.37

Example 11

Preparation of (2S)-2-(mesityloxy)-N-[4-(pyridin-2-yl)-1H-imidazol-2-yl]propanamide (Compound 11)

N-[Amino(imino)methyl]-(2S)-2-(mesityloxy)propanamide (3.0 g; 12 mmol) obtained in Synthesis Example 10 was dissolved in N,N-dimethylformamide (16 mL), 2-bromo-1-pyridin-2-ylethanone (1.3 g; 4.8 mmol) was added thereto, and the mixture was stirred for 142 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 2% methanol/chloroform), and crystallized from diethyl ether to give 220 mg of the title compound (yield 13%) expressed by the following formula (Ex. 11).

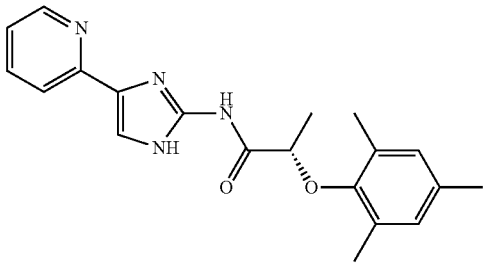

(Ex. 11)

$^1$H-NMR (d$_6$-DMSO) δ:
1.47 (3H, d, J=6.4 Hz), 2.17 (3H, s), 2.20 (6H, s), 4.59 (1H, q, J=6.4 Hz), 6.81 (2H, s), 7.17 (1H, t, J=5.7 Hz), 7.38 (1H, s), 7.70-7.77 (2H, m), 8.48 (1H, s), 11.34 (1H, br), 11.91 (1H, br)
Mass: M+1=351.35

Example 12

Preparation of 2-(mesityloxy)-2-methyl-N-[4-(pyridin-2-yl)-1H-imidazol-2-yl]propanamide (Compound 12)

N-[Amino(imino)methyl]-2-(mesityloxy)-2-methylpropanamide (2.80 g; 10.6 mmol) obtained in Synthesis Example 12 was dissolved in N,N-dimethylformamide (15 mL), 2-bromo-1-pyridin-2-ylethanone (700 mg; 3.5 mmol) was added thereto, and the mixture was stirred for 120 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 4% methanol/chloroform). The resulting oily substance was crystallized from diethyl ether to give 240 mg of the title compound (yield 19%) expressed by the following formula (Ex. 12).

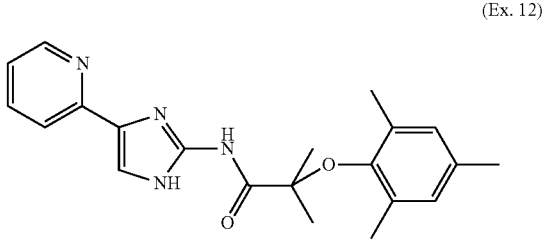 [SMILES: Cc1cc(C)c(OC(C)(C)C(=O)Nc2nc(-c3ccccn3)c[nH]2)c(C)c1]

(Ex. 12)

$^1$H-NMR (d$_6$-DMSO) δ:
1.43 (6H, s), 2.14 (6H, s), 2.18 (3H, s), 6.82 (2H, s), 7.16-7.19 (1H, m), 7.42 (1H, brs), 7.76-7.78 (2H, m), 8.49 (1H, s)
Mass: M+1=365.22

Example 13

Preparation of 2-(mesitylthio)-N-[4-(pyridin-2-yl)-1H-imidazol-2-yl]acetamide (Compound 13)

N-[Amino(imino)methyl]-2-(mesitylthio)acetamide (3.02 g; 12 mmol) obtained in Synthesis Example 14 was dissolved in N,N-dimethylformamide (15 mL), 2-bromo-1-pyridin-2-ylethanone (800 mg; 4.0 mmol) was added thereto, and the mixture was stirred for 115 hours at room temperature. To the reaction solution, ethyl acetate (250 mL) was added, and the mixture was washed with 10% aqueous sodium carbonate solution (three times). The organic layer was dried over anhydrous magnesium sulfate, and then distilled under reduced pressure. The resulting residue was separated by silica gel column (0 to 4% methanol/chloroform). The resulting crystals were dispersed in ethyl acetate, collected by filtration and dried to give 200 mg of the title compound (yield 14%) expressed by the following formula (Ex. 13).

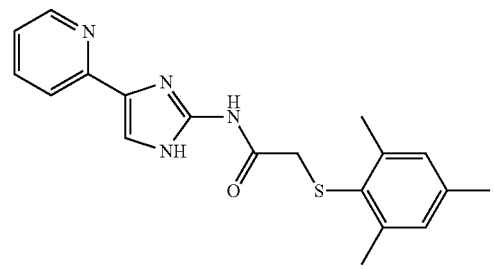

(Ex. 13)

$^1$H-NMR (d$_6$-DMSO) δ:
2.21 (3H, s), 2.44 (6H, s), 3.47 (2H, s), 6.96 (2H, s), 7.15-7.18 (1H, m), 7.32 (1H, s), 7.70-7.77 (2H, m), 8.48 (1H, s), 11.41 (1H, brs), 11.75 (1H, brs)
Mass: M+1=353.28

Example 14

Preparation of 2-[mesityl(methyl)amino]-N-[4-(pyridin-2-yl)-1H-imidazol-2-yl]acetamide (Compound 14)

N-[Amino(imino)methyl]-2-[mesityl(methyl)amino]acetamide (2.61 g; 10.5 mmol) obtained in Synthesis Example 16 was dissolved in N,N-dimethylformamide (15 mL), 2-bromo-1-pyridin-2-ylethanone (700 mg; 3.5 mmol) was added thereto, and the mixture was stirred for 42 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 4% methanol/chloroform). The resulting oily substance was crystallized from diethyl ether to give 140 mg of the title compound (yield 11%) expressed by the following formula (Ex. 14).

(Ex. 14)

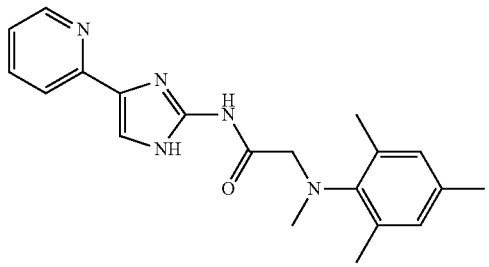

¹H-NMR (d₆-DMSO) δ:
2.17 (3H, s), 2.28 (6H, s), 2.80 (3H, s), 3.80 (2H, s), 6.80 (2H, s), 7.15-7.17 (1H, m), 7.34 (1H, s), 7.73-7.76 (2H, m), 8.48 (1H, s), 11.05 (1H, brs), 11.88 (1H, brs)

Mass: M+1=350.34

Example 15

Preparation of 3-mesityl-N-[4-(pyridin-2-yl)-1H-imidazol-2-yl]propanamide (Compound 15)

N-[Amino(imino)methyl]-3-mesitylpropanamide (5.50 g; 24 mmol) obtained in Synthesis Example 18 was dissolved in N,N-dimethylformamide (80 mL), 2-bromo-1-(pyridin-2-yl)ethanone (2.0 g; 10 mmol) was added thereto, and the mixture was stirred for 98 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 5% methanol/chloroform), and the resulting crystals were dispersed in ethyl acetate, collected by filtration and dried to give 340 mg of the title compound (yield 10%) expressed by the following formula (Ex. 15).

(Ex. 15)

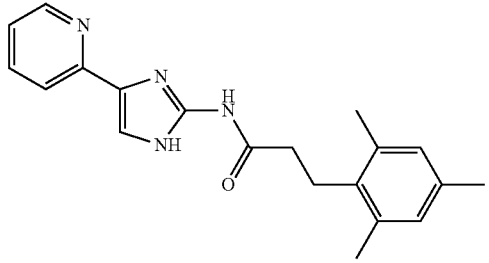

¹H-NMR (d₆-DMSO) δ:
2.18 (3H, s), 2.27 (6H, s), 2.45-2.48 (2H, m), 2.86-2.89 (2H, m), 6.81 (2H, s), 7.15-7.17 (1H, m), 7.35 (1H, s), 7.72-7.76 (2H, m), 8.48 (1H, s), 11.33 (1H, br), 11.78 (1H, br)
Mass: M+1=335.48

Example 16

Preparation of (2E)-3-mesityl-N-[4-(pyridin-2-yl)-1H-imidazol-2-yl]acrylamide (Compound 16)

(2E)-N-[Amino(imino)methyl]-3-mesitylacrylamide (3.47 g; 15 mmol) obtained in Synthesis Example 20 was dissolved in N,N-dimethylformamide (50 mL), 2-bromo-1-pyridin-2-ylethanone (1.0 g; 5 mmol) was added thereto, and the mixture was stirred for 144 hours at room temperature. To the reaction solution, ethyl acetate (200 mL) was added, and the mixture was washed with saturated aqueous sodium bicarbonate solution (three times). The organic layer was dried over anhydrous magnesium sulfate, and then distilled under reduced pressure. The resulting residue was separated by silica gel column (0 to 3% methanol/chloroform), and crystallized from ethyl acetate to give 330 mg of the title compound (yield 20%) expressed by the following formula (Ex. 16).

(Ex. 16)

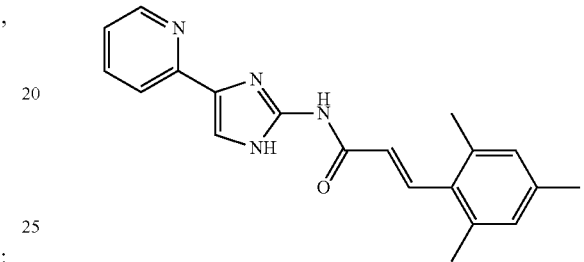

¹H-NMR (d₆-DMSO) δ:
2.25 (3H, s), 2.32 (6H, s), 6.52 (1H, d, J=16.0 Hz), 6.95 (2H, s), 7.18 (1H, t, J=5.7 Hz), 7.41 (1H, s), 7.76-7.79 (3H, m), 8.50 (1H, s), 11.57 (1H, br), 11.91 (1H, br)

Mass: M+1=333.31

Example 17

Preparation of 2-(mesityloxy)-N-[1-methyl-4-(pyridin-2-yl)-1H-imidazol-2-yl]acetamide (Compound 17) hydrochloride N-[Imino(methylamino)methyl]-2-(mesityloxy)acetamide (7.65 g; 30 mmol) obtained in Synthesis Example 22 was dissolved in N,N-dimethylformamide (60 mL), 2-bromo-1-pyridin-2-ylethanone (2.0 g; 10 mmol) was added thereto, and the mixture was stirred for 70 hours at room temperature. To the reaction solution, ethyl acetate (300 mL) was added, and the mixture was washed with saturated aqueous sodium bicarbonate solution (three times). A back extraction with 2 mol/L aqueous hydrochloric acid solution (100 mL) was performed and then the aqueous layer was adjusted to pH 9 with 10% aqueous sodium carbonate solution, and extracted with chloroform. The organic layer was dried over anhydrous magnesium sulfate, and then distilled under reduced pressure. The resulting residue was dissolved in acetonitrile (40 mL), and the mixture was heated under reflux for 22 hours. The solvent was distilled off under reduced pressure, and the resulting residue was separated by silica gel column (0 to 4% methanol/chloroform). To the resulting oily substance, 10% hydrochloric acid/methanol solution (10 mL) was added and dissolved, and then the mixture was distilled under reduced pressure. The resulting oily substance was crystallized from acetone to give 450 mg of the title compound (yield 13%) which is a salt of Compound 17 expressed by the following formula (Ex. 17).

(Ex. 17)

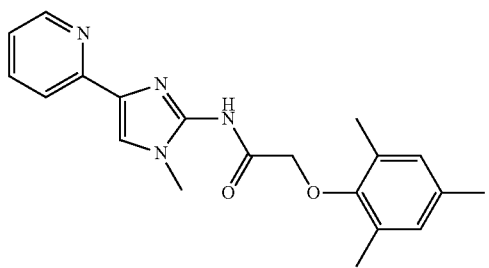

¹H-NMR (d₆-DMSO) δ:
2.21 (3H, s), 2.27 (6H, s), 3.67 (3H, s), 4.52 (2H, s), 6.87 (2H, s), 7.72 (1H, t, J=6.6 Hz), 8.26 (1H, d, J=8.2 Hz), 8.41-8.45 (1H, m), 8.47 (1H, s), 8.64 (1H, d, J=5.0 Hz), 10.83 (1H, brs)
Mass: M+1=351.26

Example 18

Preparation of 2-(mesityloxy)-N-[4-(2-nitrophenyl)-1H-imidazol-2-yl]acetamide (Compound 18)

(Mesityloxy)acetic acid (1.61 g; 8.3 mmol), diisopropylethylamine (5.37 g; 42 mmol), 2-amino-4-(2-nitrophenyl)-1H-imidazole dihydrochloride (2.0 g; 8.3 mmol) obtained in Synthesis Example 24, and 1-hydroxybenzotriazole monohydrate (1.53 g; 10 mmol) were dissolved in N,N-dimethylformamide (40 mL), 2-(1H)-benzotriazol-1-yl-1,1,3,3-tetramethyluronium hexafluorophosphate (3.78 g; 10 mmol) was added thereto, and the mixture was stirred for 39 hours at room temperature. To the reaction solution, ethyl acetate (200 mL) was added, and the mixture was washed with 10% aqueous citric acid solution, brine, and then saturated aqueous sodium bicarbonate solution. The organic layer was dried over anhydrous magnesium sulfate, and then distilled under reduced pressure. The residue was separated by silica gel column (0 to 2% methanol/chloroform). The resulting crystals were dispersed in diethyl ether, collected by filtration and dried to give 950 mg of the title compound (yield 30%) expressed by the following formula (Ex. 18).

(Ex. 18)

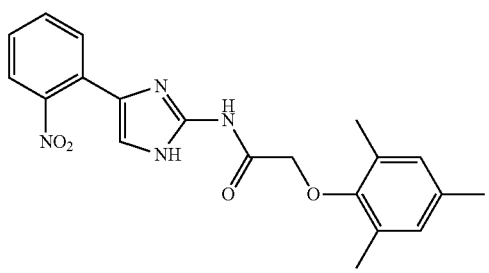

¹H-NMR (CDCl₃) δ:
2.23 (6H, s), 2.26 (3H, s), 4.40 (2H, s), 6.85 (2H, s), 7.10 (1H, s), 7.38 (1H, dt, J=1.4 Hz, 7.8 Hz), 7.56 (1H, dt, J=0.9 Hz, 7.3 Hz), 7.65 (1H, d, J=8.2 Hz), 7.80 (1H, d, J=7.8 Hz), 9.62 (1H, br), 10.88 (1H, br)
Mass: M+1=381.34

Example 19

Preparation of N-[4-(2-aminophenyl)-1H-imidazol-2-yl]-2-(mesityloxy)acetamide (Compound 19)

Iron powder (1.0 g) was suspended in 50% aqueous ethanol solution (100 mL), 12 mol/L hydrochloric acid (1.0 mL) was added thereto, and the mixture was stirred for 30 minutes at 70° C. To the mixture was added 2-(mesityloxy)-N-[4-(2-nitrophenyl)-1H-imidazol-2-yl]acetamide (Compound 18) (875 mg, 2.3 mmol) obtained in Example 18, and the mixture was stirred for 1 hour at 70° C. The mixture was left to cool, and then the insoluble materials were removed by filtration, and then the filtrate was extracted with chloroform. The organic layer was dried over anhydrous magnesium sulfate, and then distilled under reduced pressure. The resulting residue was separated by silica gel column (0 to 3% methanol/chloroform), and the resulting crystals were dispersed in diethyl ether, collected by filtration and dried to give 520 mg of the title compound (yield 65%) expressed by the following formula (Ex. 19).

(Ex. 19)

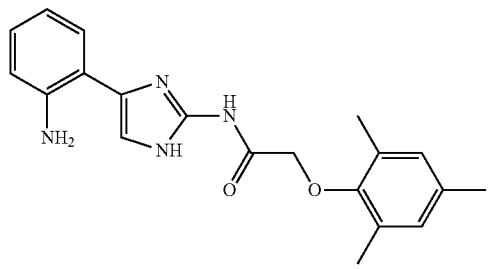

¹H-NMR (d₆-DMSO) δ:
2.19 (3H, s), 2.23 (6H, s), 4.44 (2H, s), 6.12 (2H, s), 6.50 (1H, t, J=7.3 Hz), 6.64 (1H, d, J=7.8 Hz), 6.88-6.92 (1H, m), 7.16 (1H, s), 7.40 (1H, d, J=7.3 Hz), 11.17 (1H, br), 11.88 (1H, br)
Mass: M+1=351.36

Example 20

Preparation of N-{4-[2-(acetylamino)phenyl]-1H-imidazol-2-yl}-2-(mesityloxy)acetamide (Compound 20)

To a mixed solution of acetic acid (10 mL) and acetic anhydride (5 mL), N-[4-(2-aminophenyl)-1H-imidazol-2-yl]-2-(mesityloxy)acetamide (Compound 19) (350 mg, 1.0 mmol) obtained in Example 19 was added, and the mixture was stirred for 16 hours at room temperature. The solvent was distilled off under reduced pressure, the resulting residue was dissolved in chloroform (50 mL), and the mixture was washed with 10% aqueous sodium carbonate solution. The organic layer was dried over anhydrous magnesium sulfate, and then distilled under reduced pressure. The resulting residue was dissolved in 10% ammonia/methanol solution (10 mL), and the mixture was stirred for 6 hours at room temperature. To the reaction solution, chloroform (50 mL) was added, and the mixture was washed with saturated aqueous sodium bicarbonate solution. The organic layer was dried over anhydrous magnesium sulfate, and then distilled under reduced pressure. The resulting crystals were dispersed in diethyl ether, collected by filtration and dried to give 250 mg of the title compound (yield 91%) expressed by the following formula (Ex. 20).

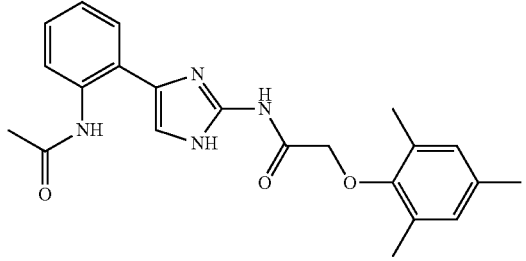

(Ex. 20)

$^1$H-NMR (d$_6$-DMSO) δ:
2.17 (3H, s), 2.20 (3H, s), 2.25 (6H, s), 4.50 (2H, s), 6.85 (2H, s), 7.03 (1H, t, J=7.6 Hz), 7.14-7.18 (1H, m), 7.41 (1H, s), 7.71 (1H, d, J=6.9 Hz), 8.36 (1H, d, J=7.6 Hz), 12.05 (1H, s)
Mass: M+1=393.29

Example 21

Preparation of 1-mesityloxy-N-[4-(pyridin-2-yl)-1H-imidazol-2-yl]cyclobutanecarboxamide (Compound 21)

1-(Mesityloxy)cyclobutanecarboxylic acid (1.34 g; 5.7 mmol), diisopropylethylamine (5.94 g; 46 mol), 2-amino-4-pyridin-2-yl-1H-imidazole trihydrochloride (1.55 g; 5.7 mmol) obtained in Synthesis Example 26 or Synthesis Example 29, and 1-hydroxybenzotriazole monohydrate (1.05 g; 6.9 mmol) were dissolved in N,N-dimethylformamide (40 mL), 2-(1H-benzotriazol-1-yl-1,1,3,3-tetramethyluronium hexafluorophosphate (2.61 g; 6.9 mmol) was added, and the mixture was stirred for 18 hours at room temperature. To the reaction solution, ethyl acetate (300 mL) was added, and the mixture was washed with saturated aqueous sodium bicarbonate solution (three times). The organic layer was dried over anhydrous magnesium sulfate, and then distilled under reduced pressure. The residue was separated by silica gel column (0 to 4% methanol/chloroform), and the resulting crystals were dispersed in ethyl acetate, collected by filtration and dried to give 450 mg of the title compound (yield 21%) expressed by the following formula (Ex. 21).

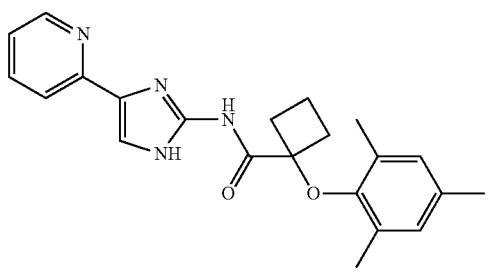

(Ex. 21)

$^1$H-NMR (d$_6$-DMSO) δ:
1.51-1.58 (1H, m), 1.67-1.72 (1H, m), 2.16 (6H, s), 2.22 (3H, s), 2.22-2.27 (2H, m), 2.45-2.49 (2H, m), 6.89 (2H, s), 7.17-7.19 (1H, m), 7.46 (1H, s), 7.76-7.78 (2H, m), 8.50 (1H, s), 10.86 (1H, br), 12.05 (1H, br)
Mass: M+1=377.36

Example 22

Preparation of 2-(mesitylamino)-N-(4-pyridin-2-yl-1H-imidazol-2-yl)acetamide (Compound 22)

(Mesitylamino)acetic acid hydrochloride (1.50 g; 6.5 mmol), diisopropylethylamine (8.06 g; 62 mol), 2-amino-4-pyridin-2-yl-1H-imidazole trihydrochloride (2.10 g; 7.8 mmol) obtained in Synthesis Example 26 or Synthesis Example 29, and 1-hydroxybenzotriazole monohydrate (1.19 g; 7.8 mmol) were dissolved in N,N-dimethylformamide (80 mL), 2-(1H-benzotriazol-1-yl)-1,1,3,3-tetramethyluronium hexafluorophosphate (2.95 g; 7.8 mmol) was added, and the mixture was stirred for 41 hours at room temperature. To the reaction solution, ethyl acetate (300 mL) was added, and the mixture was washed with saturated aqueous sodium bicarbonate solution (three times), brine, and then 10% aqueous citric acid solution. The organic layer was dried over anhydrous magnesium sulfate, and then distilled under reduced pressure. The residue was separated by silica gel column (2 to 4% methanol/chloroform), and the resulting crystals were dispersed in ethyl acetate, collected by filtration and dried to give 510 mg of the title compound (yield 23%) expressed by the following formula (Ex. 22).

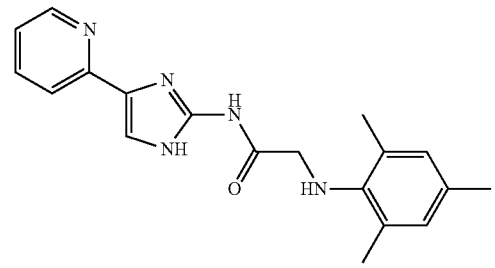

(Ex. 22)

$^1$H-NMR (d$_6$-DMSO) δ: 2.14 (3H, s), 2.24 (6H, s), 3.81 (2H, d, J=6.4 Hz), 4.31 (1H, t, J=6.4 Hz), 6.74 (2H, s), 7.17 (1H, t, J=5.5 Hz), 7.34 (1H, s), 7.71-7.77 (2H, m), 8.48 (1H, s), 11.28 (1H, br), 11.82 (1H, br)
Mass: M+1=336.31

Example 23

Preparation of 2-[(2,6-dimethylphenyl)amino]-N-[4-(pyridin-2-yl)-1H-imidazol-2-yl]acetamide (Compound 23)

[(2,6-Dimethylphenyl)amino]acetic acid hydrochloride (880 mg; 4.0 mmol), diisopropylethylamine (4.22 g; 32 mol), and 2-amino-4-pyridin-2-yl-1H-imidazole trihydrochloride (1.10 g; 4.0 mmol) obtained in Synthesis Example 26 or Synthesis Example 29 were dissolved in N,N-dimethylformamide (30 mL). 1-Hydroxybenzotriazole monohydrate (750 mg; 4.8 mmol) and 2-(1H-benzotriazol-1-yl-1,1,3,3-tetramethyluronium hexafluorophosphate (1.86 g; 4.8 mmol) were added thereto, and then the mixture was stirred for 18 hours at room temperature. To the reaction solution, ethyl acetate (300 mL) was added, and the mixture was washed with saturated aqueous sodium bicarbonate solution (three times), brine, and then 10% aqueous citric acid solution. The organic layer was dried over anhydrous magnesium sulfate, and then distilled under reduced pressure. The residue was separated by silica gel column (2 to 5% methanol/chloroform), and the resulting crystals were dispersed in ethyl acetate, collected by filtration and dried to give 370 mg of the title compound (yield 29%) expressed by the following formula (Ex. 23).

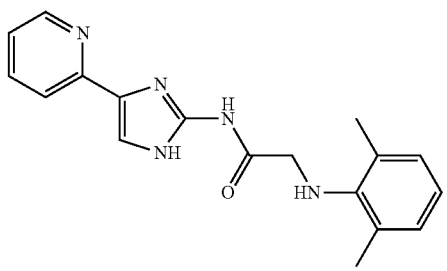

(Ex. 23)

$^1$H-NMR (d$_6$-DMSO) δ:
2.28 (6H, s), 3.89 (2H, s), 4.46 (1H, s), 6.71 (1H, t, J=7.4 Hz), 6.92 (2H, d, J=7.4 Hz), 7.17 (1H, s), 7.33 (1H, s), 7.71-7.77 (2H, m), 8.47 (1H, s), 11.30 (1H, br), 11.84 (1H, br)
Mass: M+1=322.34

Example 24

Preparation of 2-[(2,6-dimethylphenyl)amino]-N-[4-(pyridin-2-yl)-1H-imidazol-2-yl]propanamide (Compound 24)

2-[(2,6-Dimethylphenyl)amino]propionic acid hydrochloride (920 mg; 4.0 mmol), diisopropylethylamine (5.17 g; 40 mol), 2-amino-4-pyridin-2-yl-1H-imidazole trihydrochloride (1.38 g; 5.0 mmol) obtained in Synthesis Example 26 or Synthesis Example 29, and 1-hydroxybenzotriazole monohydrate (770 mg; 5.0 mmol) were dissolved in N,N-dimethylformamide (20 mL), 2-(1H-benzotriazol-1-yl)-1,1,3,3-tetramethyluronium hexafluorophosphate (1.90 g; 5.0 mmol) was added thereto, and the mixture was stirred for 89 hours at room temperature. To the reaction solution, ethyl acetate (250 mL) was added, and the mixture was washed with saturated aqueous sodium bicarbonate solution (three times), brine, and then 10% aqueous citric acid solution. The organic layer was dried over anhydrous magnesium sulfate, and then distilled under reduced pressure. The residue was separated by silica gel column (0 to 4% methanol/chloroform), and the resulting crystals were dispersed in ethyl acetate, collected by filtration and dried to give 70 mg of the title compound (yield 4%) expressed by the following formula (Ex. 24).

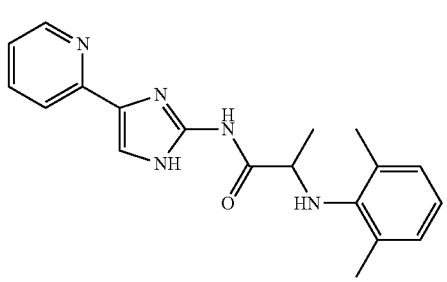

(Ex. 24)

$^1$H-NMR (d$_6$-DMSO) δ:
1.35 (3H, d, J=6.8 Hz), 2.28 (6H, s), 4.03-4.09 (1H, m), 4.22 (1H, d, J=10.9 Hz), 6.72 (1H, t, J=7.2 Hz), 6.92 (2H, d, J=7.2 Hz), 7.15-7.17 (1H, m), 7.33 (1H, s), 7.68-7.76 (2H, m), 8.47 (1H, s), 11.34 (1H, br), 11.81 (1H, br)
Mass: M+1=336.41

Example 25

Preparation of (2R)-2-(mesityloxy)-N-[4-(pyridin-2-yl)-1H-imidazol-2-yl]propanamide (Compound 10) dihydrochloride (2R)-2-(Mesityloxy)-N-(4-pyridin-2-yl-1H-imidazol-2-yl)propanamide (Compound 10) (4.1 g, 11.7 mmol) obtained in Example 10 was dissolved in 10% hydrochloric acid/methanol solution (70 mL), and the solvent was distilled off under reduced pressure. The resulting crystals were dispersed in acetone, collected by filtration and dried to give 4.4 g of the title compound (yield 89%) which is a salt of Compound 10.
$^1$H-NMR (d$_6$-DMSO) δ:
1.47 (3H, d, J=6.6 Hz), 2.18 (3H, s), 2.22 (6H, s), 4.71 (1H, q, J=6.6 Hz), 6.83 (2H, s), 7.66-7.69 (1H, m), 8.21-8.23 (1H, m), 8.33 (1H, s), 8.34-8.37 (1H, m), 8.63-8.65 (1H, m), 11.65 (1H, s)
Mass: M+1=351.22

Example 26

Preparation of 2-[mesityl(methyl)amino]-N-[4-(pyridin-2-yl)-1H-imidazol-2-yl]acetamide (Compound 14) trihydrochloride 2-[Mesityl(methyl)amino]-N-(4-pyridin-2-yl-1H-imidazol-2-yl)acetamide (Compound 14) (4.1 g, 12.0 mmol) obtained in Example 14 was dissolved in 10% hydrochloric acid/methanol solution (50 mL), and the solvent was distilled off under reduced pressure. The resulting oily substance was crystallized from acetone, collected by filtration and dried to give 5.0 g of the title compound (yield 91%) which is a salt of Compound 14.
$^1$H-NMR (d$_6$-DMSO) δ:
2.18 (3H, s), 2.30 (6H, s), 2.82 (3H, s), 3.91 (2H, s), 6.82 (2H, s), 7.65-7.68 (1H, m), 8.23 (1H, d, J=8.3 Hz), 8.27 (1H, s), 8.32-8.35 (1H, m), 8.63-8.65 (1H, m), 11.35 (1H, s)
Mass: M+1=350.26

Example 27

Preparation of 2-(mesityloxy)-2-methyl-N-[4-(pyridin-2-yl)-1H-imidazol-2-yl]propanamide (Compound 12) dihydrochloride 2-(Mesityloxy)-2-methyl-N-(4-pyridin-2-yl-1H-imidazol-2-yl)propanamide (Compound 12) (4.7 g, 12.9 mmol) obtained in Example 12 was dissolved in 10% hydrochloric acid/methanol solution (70 mL), and the solvent was distilled off under reduced pressure. The resulting oily substance was crystallized from acetone, collected by filtration and dried to give 5.3 g of the title compound (yield 94%) which is a salt of Compound 12.
$^1$H-NMR (d$_6$-DMSO) δ:
1.46 (6H, s), 2.16 (6H, s), 2.20 (3H, s), 6.85 (2H, s), 7.59-7.62 (1H, m), 8.19-8.26 (2H, m), 8.30 (1H, s), 8.65 (1H, d, J=5.4 Hz), 11.72 (1H, s)
Mass: M+1=365.18

Example 28

Preparation of 2-(mesitylamino)-N-[4-(pyridin-2-yl)-1H-imidazol-2-yl]acetamide (Compound 22) trihydrochloride 2-(Mesitylamino)-N-(4-pyridin-2-yl-1H-imidazol-2-yl) acetamide (Compound 22) (2.40 g, 7.2 mmol) obtained in Example 22 was dissolved in 10% hydrochloric acid/methanol (30 mL), and the solvent was distilled off under reduced pressure. The resulting crystals were dispersed in acetone, collected by filtration and dried to give 3.0 g of the title compound (yield 94%) which is a salt of Compound 22.

$^1$H-NMR ($d_6$-DMSO) δ:
2.18 (3H, s), 2.32 (6H, s), 4.03 (2H, s), 6.84 (2H, s), 7.67 (1H, ddd, J=1.2 Hz, 5.7 Hz, 7.5 Hz), 8.24 (1H, d, J=7.5 Hz), 8.25 (1H, s), 8.35 (1H, dt, J=1.2 Hz, 8.3 Hz), 8.63 (1H, d, J=5.7 Hz)
Mass: M+1=336.24

Example 29

Preparation of (2S)-2-(mesityloxy)-N-[4-(pyridin-2-yl)-1H-imidazol-2-yl]propanamide (Compound 11) dihydrochloride (2S)-2-(Mesityloxy)-N-(4-pyridin-2-yl-1H-imidazol-2-yl)propanamide (Compound 11) (3.50 g, 10.0 mmol) obtained in Example 11 was dissolved in 10% hydrochloric acid/methanol (60 mL), and the solvent was distilled off under reduced pressure. The resulting crystals were dispersed in acetone, collected by filtration and dried to give 3.96 g of the title compound (yield 94%) which is a salt of Compound 11.

$^1$H-NMR ($d_6$-DMSO) δ:
1.47 (3H, d, J=6.7 Hz), 2.19 (3H, s), 2.22 (6H, s), 4.71 (1H, q, J=6.7 Hz), 6.84 (2H, s), 7.67 (1H, ddd, J=1.2 Hz, 5.6 Hz, 7.3 Hz), 8.22 (1H, dt, J=1.2 Hz, 8.3 Hz), 8.31 (1H, s), 8.35 (1H, dd, J=1.7 Hz, 8.3 Hz), 8.64 (1H, d, J=5.6 Hz), 11.62 (1H, brs)
Mass: M+1=351.21

Example 30

Preparation of 2-(2,6-dimethylphenoxy)-N-[4-(pyridin-2-yl)-1H-imidazol-2-yl]acetamide (Compound 8) dihydrochloride 2-(2,6-Dimethylphenoxy)-N-(4-pyridin-2-yl-1H-imidazol-2-yl)acetamide (Compound 8) (5.40 g, 16.8 mmol) obtained in Example 8 was dissolved in 10% hydrochloric acid/methanol solution (30 mL), and the solvent was distilled off under reduced pressure. The resulting crystals were dispersed in acetone, collected by filtration and dried to give 6.05 g of the title compound (yield 91%) which is a salt of Compound 8.

$^1$H-NMR ($d_6$-DMSO) δ:
2.29 (6H, s), 4.59 (2H, s), 6.98 (1H, t, J=7.6 Hz), 7.06 (2H, d, J=7.6 Hz), 7.66-7.69 (1H, m), 8.25 (1H, d, J=7.8 Hz), 8.32 (1H, s), 8.33-8.37 (1H, m), 8.65 (1H, d, J=4.6 Hz), 11.62 (1H, s)
Mass: M+1=323.24

[Evaluation Test]

The acylaminoimidazole derivatives (I) (compound 10, compound 11, compound 12, compound 14 and compound 22) of the present invention obtained in Examples 10, 11, 12, 14 and 22 were examined for blood-brain barrier permeability, suppressive activity of oxidative stress-mediated cell death, solubility and administration test using a model animal. The results are shown in the following Test Examples 1 to 4. As comparative compounds, a compound (X) (2-(mesityloxy)-N-(4-pyridin-2-yl-1,3-thiazol-2-yl)acetamide) represented by the formula (X) described in International Publication No. WO 2008/050600 and a compound (1e) obtained in Comparative Example 1 were used

Experimental Example 1

Evaluation of Blood-Brain Barrier Permeability

For evaluation of blood-brain barrier permeability, pharmacokinetics (the concentration in brain) in mice was analyzed. In the test, male C57BL/6N mice (at 8 weeks of age) were used. Each compound was suspended in 0.5% sodium carboxymethylcellulose (CMC-Na). The dosage amount was 100 mg/kg per body weight of each mouse. Each compound was administered once orally under fasting conditions. At the time points of 30 minutes and one hour after administration, blood was collected from the heart of each mouse. Subsequently, perfusion was performed using physiological saline containing 10% heparin and thereafter the brain was removed. Serum was obtained by centrifuging the blood sample and brain was lyophilized with liquid nitrogen, both of which were stored at −80° C. until use.

Next, as a pre-treatment for HPLC analysis, deproteinization treatment was performed. Acetonitrile was added to the brain sample and homogenization treatment was performed to grind the brain. The resultant sample was centrifuged (10,000×g, 10 min, 4° C.) and the supernatant was collected, allowed to stand still at −80° C. for 10 minutes, thawed and then centrifuged again (10,000×g, 10 min, 4° C.). The obtained supernatant was dried under vacuum. The vacuum-dried sample was dissolved in a 10 mM phosphate buffer (pH7.0) containing 30-50% acetonitrile, allowed to stand still at −80° C. for 10 minute, thawed again and centrifuged at (10,000×g, 10 min, 4° C.) and the supernatant was collected. Furthermore, filtration treatment by a 0.45 μm filter and centrifugation (10,000×g, 4 min, 4° C.) were performed and subsequently filtration treatment by a 0.22 μm filter and centrifugation (10,000×g, 4 min, 4° C.) were performed. The supernatant was then collected and subjected to HPLC analysis. A standard curve was prepared by using the brain of the same type mouse to which none of the compounds was administered.

HPLC analysis conditions will be described below.
Apparatus: SHIMAZU LC-10
Column: CAPCELL PAK C18, 4.6 mm I.D.×150 mm (SHISEIDO)
Eluate: 10 mM phosphate buffer/acetonitrile (30-50%)
Flow rate: 1.0 ml/min
Detection: UV 320/260 nm (SPD-10Ai)
Dilution solution: 10 mM phosphate buffer/acetonitrile (30-50%)
Sample amount: 100 μl
The obtained results are shown in Table 1.

TABLE 1

| | Amount of blood brain barrier permeation |
|---|---|
| Comparative compound: Compound (X) | 62/26 |
| Comparative compound: Compound (Ie) | 27/8 |
| Compound 10 | 256/225 |

TABLE 1-continued

| | Amount of blood brain barrier permeation |
|---|---|
| Compound 11 | 478/372 |
| Compound 12 | 258/133 |
| Compound 14 | 519/370 |
| Compound 22 | 108/16 |

Unit: (ng/100 μg, 0.5 h/1 h)

From the above results, it is found that compound (Ie) obtained by only converting a thiazole group of compound (X) into an imidazole group significantly reduces in blood-brain barrier permeability. Compared to this, compound 10, compound 11, compound 12, compound 14 and compound 22, which are obtained by converting the thiazole group of compound (X) into an imidazole group and introducing a predetermined substituent, are extremely improved in blood-brain barrier permeability.

Experimental Example 2

Analysis of Oxidative Stress-Mediated Cell Death in Differentiated Nerve Cells

A test was performed by using the same compounds as in Test Example 1. Human neuroblastoma SH-SY5Y cells (ATCC, CRL2266 strain) were cultured in DMEM medium (manufactured by Wako Pure Chemical Industries Ltd.) containing 10% FBS, 100 μg/mL streptomycin and 100 U/mL penicillin G. SH-SY5Y cells were suspended in a DMEM/10% FBS medium, seeded in a cell density of $0.75 \times 10^4$ cells/well in a 96-well microplate and cultured in the presence of 5% $CO_2$ at 37° C. for 24 hours. Thereafter, the medium was exchanged with DMEM/10% FBS (DMEM/FBS/RA) medium containing 10 μM all-trans-retinoic acid (RA). At the fifth day, each compound was added so as to obtain 2, 4, 6, 8, 10, 20, 30, 40, 50, 60, 80 μM (final concentration) and culture was performed. Note that, in this experiment, a sample in which DMSO alone was added was used as a negative control.

After 24 hours, an oxidative stress agent, menadione, was added so as to obtain a final concentration of 0, 30, 40, 60 and 80 μM and culture was continued in the presence of 5% $CO_2$ at 37° C. (oxidative stress treatment) Cells treated with a 0.1% Triton X-100/DMEM/FBS/RA medium in place of menadione was used as a blank in this assay. After an oxidative stress treatment for 4 hours, the medium was replaced with a medium containing 10% AlamarBlue and culture was performed in the presence of 5% $CO_2$ at 37° C. Twelve hours later, fluorescent was measured at an excitation wavelength of 530 nm/detection wavelength of 580 nm by use of CYTOF-LUOR (registered trade mark) Multi-Well Plate Reader Series 4000 to quantify oxidative stress-mediated cell death suppressive (AOSCD) activity. In accordance with a conventional method, $ED_{50}$ (Effective Dose) (μM) was calculated.

The obtained results are shown in Table 2.

TABLE 2

| | $ED_{50}$ (μM) |
|---|---|
| Comparative compound: Compound (X) | 20 |
| Comparative compound: Compound (Ie) | 6 |
| Compound 10 | 8 |
| Compound 11 | 4 |
| Compound 12 | 4 |
| Compound 14 | 4 |
| Compound 22 | 21 |

From the above results, it is found that compound 10, compound 11, compound 12, compound 14 and compound 22 each exhibit a suppressive effect against cell death mediated by oxidation stress, which is equal to or stronger than those of the comparative compounds.

Experimental Example 3

Evaluation of Solubility

Using the same compounds as in Experimental Example 1, solubility in the 1st fluid (pH1.2) of the Japanese pharmacopeia was measured. The 1st fluid of the Japanese Pharmacopeia was prepared by dissolving sodium chloride in hydrochloric acid (7.0 mL) and water and adjusting the total amount to 1000 mL. The 1st fluid of the Japanese Pharmacopeia (0.6 mL) was poured in a tube and a compound was added until a precipitate was observed. Then, the tube was shaken at 25° C. for 24 hours (200 rotations/minute) to obtain a compound solution. The compound solution was added to a 96-well plate to which a 0.22 μm filter (manufactured by Millipore) was set and centrifugally filtrated (2700 rotations/minute, 10 minutes). Thereafter, the concentration of the compound in the filtrate was obtained from the peak area obtained by HPLC analysis. The solution for a calibration curve was prepared by dissolving a compound in DMSO.

HPLC analysis conditions will be described below.
Apparatus: SHIMAZU LC-10
Column: TSKgel ODS-80Tm, 4.6×150 mm (manufactured by Tohso Corporation)
Column temperature: 40° C.
Injection amount: 10 μL
Detection: UV 280 nm
Mobile phase: 20 mM sodium 1-decanesulfonate, 40 mM phosphoric acid, 0.2% trimethylamine/acetonitrile The obtained results are shown in Table 3.

TABLE 3

| | Solubility (mg/mL) |
|---|---|
| Comparative compound: Compound (X) | 0.03 |
| Comparative compound: Compound (Ie) | 0.61 |
| Compound 10 | 7.88 |
| Compound 11 | 7.98 |
| Compound 12 | 3.76 |
| Compound 14 | 3.07 |
| Compound 22 | 1.81 |

From the above results, it is found that compound 10, compound 11, compound 12, compound 14 and compound 22 are greatly improved in solubility compared to the comparative compounds.

Experimental Example 4

In Vivo Drug Efficacy Test

In this test, ALS-SOD1$^{H46R}$ transgenic mice carrying and expressing ALS1 pathological SOD1 gene (SOD1$^{H46R}$) were used. The mice were housed at 23° C. with a 12 hours light/dark cycle. Using each of the compounds (compound 10, compound 12 and compound 14) obtained in Examples 10, 12 and 14, administration of a compound was started at the time point (onset) when a neurological sign (grade 3 described later) was observed in a balance beam test (beam walking test) of ALS-SOD1$^{H46R}$ transgenic mice. Each compound was dissolved in sterilized water, and subsequently an administration solution was prepared with physiological saline. The dose of each compound was 0.01 mg, 0.1 mg and 1 mg/5 ml/kg per body weight of each individual and the compounds were orally administered once per day until an individual dies (compound-administered group). Mice to which physiological saline (5 ml/kg) alone was administered were used as a control group. As an evaluation method for expression of a neurological sign, a balance beam test (a stainless steel bar of 50 cm in length and 0.9 cm in width) was used.

As an evaluation criteria, 5 grades as shown in the following Table 4 were defined. Each of the mice was subjected to the test and grade 3 was determined as onset of disease. The motor function of the mice in the compound-administered groups and the control group was evaluated based on a vertical pole test and footprint analysis.

TABLE 4

| | |
|---|---|
| Grade 5 | Walk on the bar without slipping hind limb |
| Grade 4 | Walk on the bar although slipping hind limb sometimes |
| Grade 3 | Walk somehow on the bar although slipping hind limb frequently |
| Grade 2 | Walk a few steps from start and fall down |
| Grade 1 | Unable to stay on the bar. |

The vertical pole test (stainless steel bar of 50 cm in length and 0.9 cm in width was used) was started when the test mice became 17 weeks of age and carried out once a week. Each mouse was given five trials (noted that a maximum value was 45 cm, and when a mouse reached the vertical ascending distance of 45 cm, the trial was terminated at that point). The maximum value of the 5 trials was defined as motor function value.

Mice of the administered groups and the control group were subject to footprint analysis at 18 weeks and 22 weeks of age. Blue ink and red ink were applied respectively to the front and hind paws of the test mouse and the mouse was then allowed to walk on paper. From the footprint, irregularity of walking was observed. Data was analyzed by use of Graph-Pad Prism 5 and SPSS 17.0.

The evaluation results on the retaining ability of the motor function by the vertical pole test in ALS-SOD1$^{H46R}$ transgenic mice are shown in FIG. 1. In this evaluation, no difference was observed in the motor function among the compound 10-administered group (0.1 mg/kg) (n=6), compound 12-administered group (0.01 mg/kg) (n=6), compound 14-administered group (0.01 mg/kg) (n=6) and control group (n=5) at 17 weeks of age. In contrast, it was confirmed that the motor function was relatively retained in mouse groups administered with the compound 10, the compound 12, and the compound 14 at 21 weeks of age, as compared with at 17 weeks of age; however, the motor function was significantly reduced in the control group at 21 weeks of age.

Figure 2:
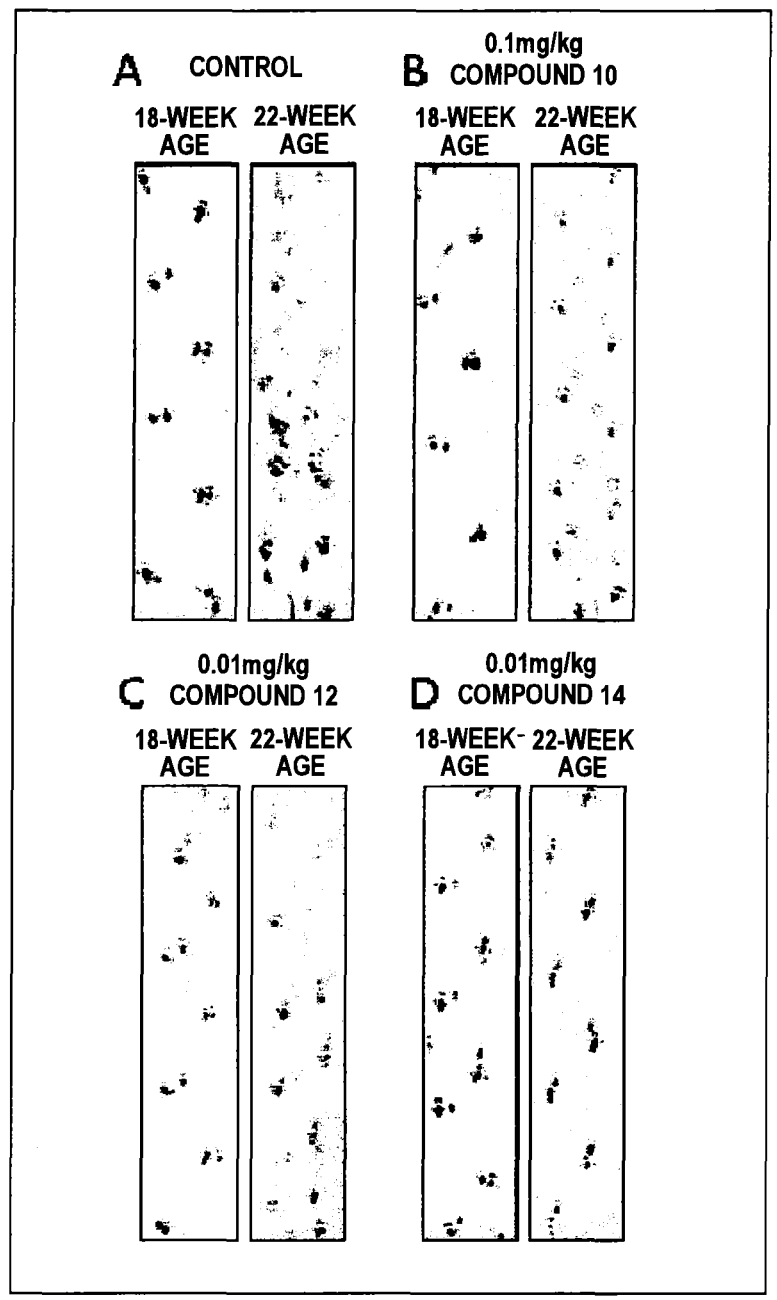
FIG. 2 is a graph showing the results of footprint analysis in ALS-SOD1$^{H46R}$ mice to which compound 10, compound 12 and compound 14 were administered. A, B, C, and D indicate the administration results for control, compound 10, compound 12 and compound 14, respectively.

The evaluation results on the retaining ability of the motor function by footprint analysis in ALS-SOD1$^{H46R}$ transgenic mice are shown in FIG. 2. In this evaluation, there was no difference of ambulation among the compound 10-administered mouse (0.1 mg/kg), the compound 12-administered mouse (0.01 mg/kg), the compound 14-administered mouse (0.01 mg/kg) and control mouse (administration of physiological saline) at 18 weeks of age. In contrast, it was confirmed that no significant change of ambulation was observed among the compound 10-administered mouse, the compound 12-administered mouse and the compound 14-administered mouse at 22 weeks of age, as compared with at 18 weeks of age; however, abnormal ambulation like dragging hind limbs was observed in the control mouse at 22 weeks of age.

From these results, it was demonstrated that the quality of life (QOL) was improved by administration of compound 10, compound 12 and compound 14.

Figure 3:
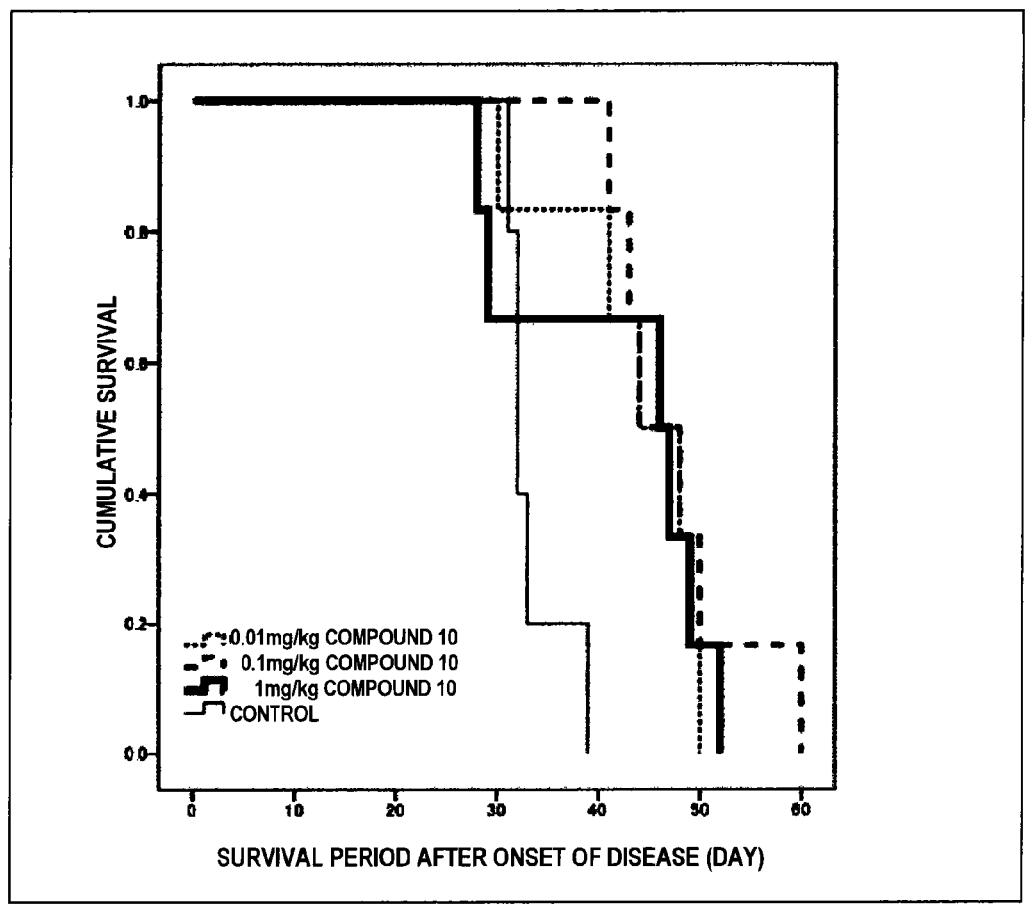
FIG. 3 is a graph showing survival period after the onset of disease (Kaplan-Meier curve) in ALS-SOD1$^{H46R}$ mice to which compound 10 was administered after the onset.
Figure 4:
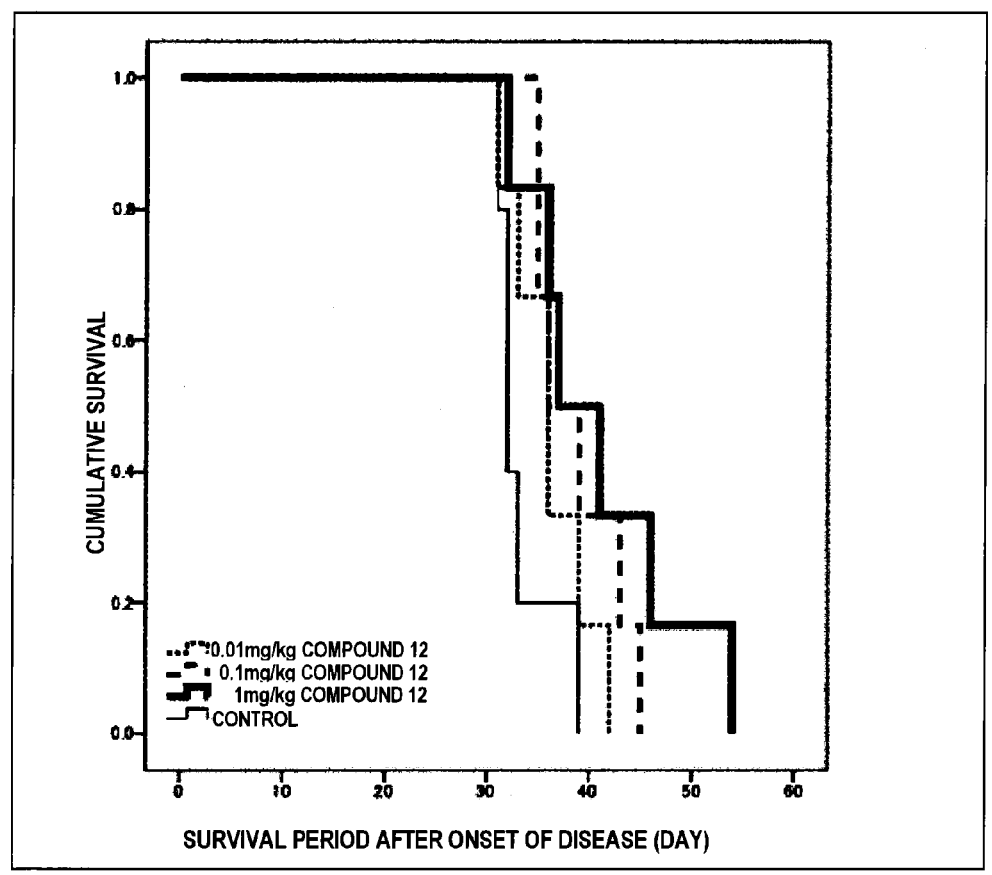
FIG. 4 is a graph showing survival period after the onset of disease (Kaplan-Meier curve) in ALS-SOD1$^{H46R}$ mice to which compound 12 was administered after the onset.
Figure 5:
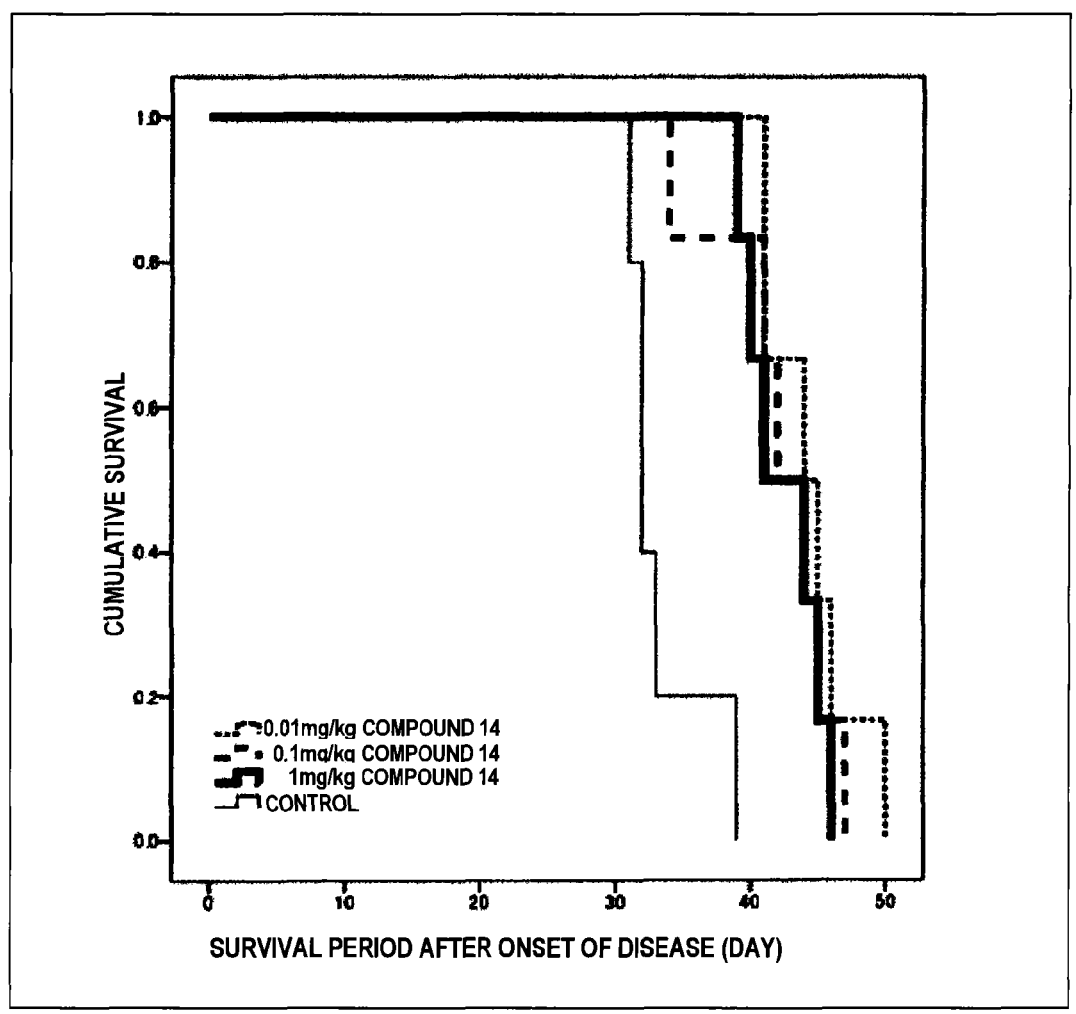
FIG. 5 is a graph showing survival period after the onset of disease (Kaplan-Meier curve) in ALS-SOD1$^{H46R}$ mice to which compound 14 was administered after the onset.

The survival period after the onset of disease in mouse groups administered each compound (onset date: 126.4±3.0 days) are shown in FIG. 3 to FIG. 5. The control-administered group showed 33.4±3.2 days (n=5); the compound 10-administered group showed 43.7±7.5 days (n=6) (0.01 mg/kg), 47.7±6.9 days (n=6) (0.1 mg/kg) and 41.8±10.5 days (n=6) (1 mg/kg); the compound 12-administered group showed 36.2±4.0 days (n=6) (0.01 mg/kg), 38.8±4.3 days (n=6) (0.1 mg/kg) and 41.0±7.9 days (n=6) (1 mg/kg); and the compound 14-administered group showed 44.5±3.4 days (n=6) (0.01 mg/kg), 42.2±4.5 days (n=6) (0.1 mg/kg) and 42.5±2.9 days (n=6) (1 mg/kg). As described above, significant survival benefit was observed in groups administered with compound 10, compound 12 and compound 14.

The invention claimed is:

1. A compound of formula (I), or a salt thereof:

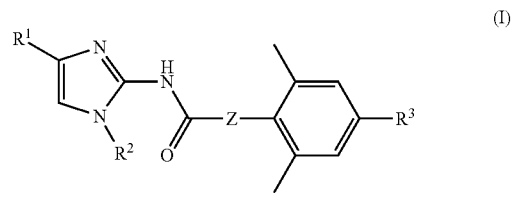

wherein
R$^1$ is a group of formula (Ia) or (Ib):

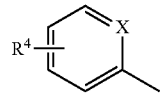

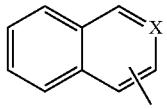

R$^4$ is a hydrogen atom, a hydroxy group, a nitro group, an optionally substituted amino group, an alkyl group or alkoxy group comprising 1 to 6 carbon atoms, an optionally substituted aryl group, an aralkyl group or an aralkyloxy group; and X is —CH— or a nitrogen atom, R$^2$ and R$^3$ are each independently a hydrogen atom or an alkyl group comprising 1 to 6 carbon atoms, Z is a group of formula (Ic) or (Id):

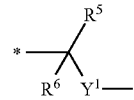

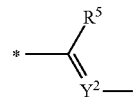

R$^5$ and R$^6$ are each independently a hydrogen atom or an alkyl group comprising 1 to 6 carbon atoms, in which R$^5$ and R$^6$ may be joined together to form a 3 to 6-membered ring;

Y$^1$ is an oxygen atom, a sulfur atom, —CH$_2$— or —NR$^7$— in which R$^7$ is a hydrogen atom or an alkyl group comprising 1 to 6 carbon atoms;

Y$^2$ is a nitrogen atom or —CH—; and

* is a site binding to a carbonyl group, with the proviso that a compound wherein R$^1$ is a group of formula (Ia), R$^2$ is a hydrogen atom, R$^3$ is a methyl group and Z is a group of formula (Ic); in formula (Ia), R$^4$ is a hydrogen atom and X is a nitrogen atom; and in formula (Ic), Y$^1$ is an oxygen atom and R$^5$ and R$^6$ are hydrogen atoms, is excluded.

2. The compound or a salt thereof according to claim 1, wherein R$^1$ is a group of formula (Ia), R$^4$ is a hydrogen atom and X is a nitrogen atom.

3. The compound or a salt thereof according to claim 1, which is (2R)-2-(mesityloxy)-N-[4-(pyridin-2-yl)-1H-imidazol-2-yl]propanamide.

4. The compound or a salt thereof according to claim 1, which is 2-(mesitylamino)-N-[4-(pyridin-2-yl)-1H-imidazol-2-yl]acetamide.

5. The compound or a salt thereof according to claim 1, which is 2-[mesityl(methyl)amino]-N-[4-(pyridin-2-yl)-1H-imidazol-2-yl]acetamide.

6. A composition, comprising the compound or a salt thereof according to claim 1 and a pharmaceutically acceptable carrier.

7. A composition, comprising the compound or a salt thereof according to claim 2 and a pharmaceutically acceptable carrier.

8. A composition, comprising the compound or a salt thereof according to claim 3 and a pharmaceutically acceptable carrier.

9. A composition, comprising the compound or a salt thereof according to claim 4 and a pharmaceutically acceptable carrier.

10. A composition, comprising the compound or a salt thereof according to claim 5 and a pharmaceutically acceptable carrier.

11. A method of inhibiting oxidative stress-mediated neural cell death in a subject in need thereof, the method comprising administering the compound or salt thereof according to claim 1 to the subject.

12. A method of inhibiting oxidative stress-mediated neural cell death in a subject in need thereof, the method comprising administering the compound or salt thereof according to claim 2 to the subject.

13. A method of inhibiting oxidative stress-mediated neural cell death in a subject in need thereof, the method comprising administering the compound or salt thereof according to claim 3 to the subject.

14. A method of inhibiting oxidative stress-mediated neural cell death in a subject in need thereof, the method comprising administering the compound or salt thereof according to claim 4 to the subject.

15. A method of inhibiting oxidative stress-mediated neural cell death in a subject in need thereof, the method comprising administering the compound or salt thereof according to claim 5 to the subject.

* * * * *